US011229613B2

(12) United States Patent
Rawas-Qalaji et al.

(10) Patent No.: US 11,229,613 B2
(45) Date of Patent: Jan. 25, 2022

(54) COMPOSITIONS INCLUDING EPINEPHRINE MICROCRYSTALS

(71) Applicant: NOVA SOUTHEASTERN UNIVERSITY, Fort Lauderdale, FL (US)

(72) Inventors: Mutasem Rawas-Qalaji, Fort Lauderdale, FL (US); Ousama Rachid, Winnipeg (CA); Keith Simons, Winnipeg (CA); Estelle Simons, Winnipeg (CA)

(73) Assignee: Nova Southeastern University, Fort Lauderdale, FL (US)

( * ) Notice: Subject to any disclaimer, the term of this patent is extended or adjusted under 35 U.S.C. 154(b) by 0 days.

(21) Appl. No.: 16/225,609

(22) Filed: Dec. 19, 2018

(65) Prior Publication Data

US 2019/0125698 A1   May 2, 2019

Related U.S. Application Data

(63) Continuation of application No. 15/288,745, filed on Oct. 7, 2016, now Pat. No. 10,159,656, which is a continuation of application No. 14/778,887, filed as application No. PCT/US2014/031579 on Mar. 24, 2014, now abandoned.

(60) Provisional application No. 61/804,892, filed on Mar. 25, 2013, provisional application No. 61/804,519, filed on Mar. 22, 2013.

(51) Int. Cl.
A61K 9/56 (2006.01)
A61K 31/137 (2006.01)
A61K 9/00 (2006.01)
A61K 9/14 (2006.01)
A61K 31/00 (2006.01)
A61K 47/12 (2006.01)
A61K 47/26 (2006.01)

(52) U.S. Cl.
CPC .......... A61K 31/137 (2013.01); A61K 9/006 (2013.01); A61K 9/0056 (2013.01); A61K 9/14 (2013.01); A61K 31/00 (2013.01); A61K 47/12 (2013.01); A61K 47/26 (2013.01)

(58) Field of Classification Search
CPC ........ A61K 31/137; A61K 31/00; A61K 9/14; A61K 9/006; A61K 9/0056; A61K 47/12; A61K 47/26
See application file for complete search history.

(56) References Cited

U.S. PATENT DOCUMENTS

| 5,143,731 A | 9/1992 | Viegas |
| 5,223,614 A | 6/1993 | Schromm et al. |
| 5,567,439 A | 10/1996 | Myers et al. |
| 5,587,172 A | 12/1996 | Cherukuri et al. |
| 5,622,716 A | 4/1997 | Barth |
| 5,622,717 A | 4/1997 | Fuisz |
| 5,654,003 A | 8/1997 | Fuisz et al. |
| 5,871,781 A | 2/1999 | Myers et al. |
| 6,024,981 A | 2/2000 | Khankari et al. |
| 6,221,392 B1 | 4/2001 | Khankari et al. |
| 6,264,981 B1 | 7/2001 | Zhang et al. |
| 6,309,663 B1 | 10/2001 | Patel et al. |
| 6,368,625 B1 | 4/2002 | Siebert et al. |
| 6,833,377 B2 | 12/2004 | Serdyuk |
| 9,877,921 B2 | 1/2018 | Rawas-Qalaji et al. |
| 10,159,656 B2 | 12/2018 | Rawas-Qalaji et al. |
| 10,568,836 B2 | 2/2020 | Rawas-Qalaji |
| 2003/0021841 A1 | 1/2003 | Matharu et al. |
| 2003/0216413 A1 | 11/2003 | Root-Bernstein et al. |
| 2004/0076588 A1 | 4/2004 | Balycky |
| 2004/0234611 A1 | 11/2004 | Ahiheim |
| 2005/0130935 A1 | 6/2005 | Weidner |
| 2006/0093677 A1 | 5/2006 | Chickering |
| 2007/0059361 A1* | 3/2007 | Rawas-Qalaji ...... A61K 9/0056 424/464 |
| 2007/0092553 A1 | 4/2007 | Tengler |
| 2007/0122465 A1 | 5/2007 | Desai |
| 2007/0154549 A1 | 7/2007 | Morton et al. |
| 2007/0202163 A1 | 8/2007 | Rawas-Qalaji et al. |

(Continued)

FOREIGN PATENT DOCUMENTS

CN   101669917   3/2010
CN   104666401   6/2015

(Continued)

OTHER PUBLICATIONS

Definition of "microcrystal" by Merriam-Webster, downloaded from https://www.merriam-webster.com/dictionary/microcrystal on Sep. 26, 2019. (Year: 2019).*
Definition of "microcrystal" by Collins, downloaded from https://www.collinsdictionary.com/us/dictionary/english/microparticle on Oct. 3, 2019. (Year: 2019).*
Qalaji, et al, title: sublingual diffusion of epinephrine microcrystals (Epi) from rapidly disintegrating tablets for the potential first-aid treatment of anaphylaxis: in vitro and ex vivo study, AAPS PharmSciTech. Oct. 2015; vol. 16, issue 5; pp. 1203-1212; published online Mar. 4, 2015 (Year: 2015).*

(Continued)

Primary Examiner — Yanzhi Zhang
(74) Attorney, Agent, or Firm — Fleit Intellectual Property Law; Paul D. Bianco; Katharine Davis

(57) ABSTRACT

The invention provides compositions including epinephrine fine particles, including epinephrine nanoparticles or nanocrystals and epinephrine microparticles or microcrystals, and methods for therapeutic use of the compositions for the treatment of conditions responsive to epinephrine such as a cardiac event or an allergic reaction, particularly anaphylaxis. The epinephrine fine particles can be incorporated into orally-disintegrating and fast-disintegrating tablet pharmaceutical formulations and can significantly increase the sublingual bioavailability of epinephrine, and thereby reduce the epinephrine dose required.

12 Claims, 11 Drawing Sheets

(56) References Cited

U.S. PATENT DOCUMENTS

| | | |
|---|---|---|
| 2007/0293580 A1 | 12/2007 | Hill |
| 2008/0032934 A1 | 2/2008 | Ellis-Behnke |
| 2008/0069779 A1 | 3/2008 | Tamarkin et al. |
| 2009/0263476 A1 | 10/2009 | Jobodevairkkam |
| 2010/0035800 A1 | 2/2010 | Desai et al. |
| 2011/0097284 A1 | 4/2011 | Bottner et al. |
| 2011/0182005 A1 | 7/2011 | Yuan |
| 2011/0182805 A1 | 7/2011 | Desimone |
| 2011/0223203 A1 | 9/2011 | Berkland et al. |
| 2011/0250278 A1 | 10/2011 | Yuan |
| 2012/0322884 A1* | 12/2012 | Rawas-Qalaji ........ A61K 9/006 514/653 |
| 2014/0242177 A1 | 8/2014 | Rawas-Qaiaji |
| 2014/0364513 A1 | 12/2014 | Park et al. |
| 2015/0164827 A1 | 6/2015 | Rawas-Qalaji et al. |
| 2016/0045457 A1 | 2/2016 | Rawas-Qalaji |
| 2016/0374966 A1 | 12/2016 | Rawas-Qalaji et al. |
| 2017/0000735 A1 | 1/2017 | Rawas-Qalaji et al. |
| 2017/0020827 A1 | 1/2017 | Rawas-Qalaji |
| 2017/0071881 A1 | 3/2017 | Rawas-Qalaji et al. |
| 2018/0110763 A1 | 4/2018 | Dutt et al. |
| 2018/0147145 A1 | 5/2018 | Rawas-Qalaji et al. |
| 2019/0125698 A1 | 5/2019 | Rawas-Qalaji |
| 2019/0231716 A1 | 8/2019 | Rawas-Qalaji |

FOREIGN PATENT DOCUMENTS

| | | |
|---|---|---|
| EP | 0159237 | 10/1985 |
| EP | 2753321 A1 | 7/2014 |
| EP | 2976072 | 5/2021 |
| WO | 1994/09762 | 11/1993 |
| WO | 2005/63203 | 12/2004 |
| WO | 2007/028247 | 3/2007 |
| WO | 2007/028247 A1 | 3/2007 |
| WO | 2007/143674 A2 | 12/2007 |
| WO | 2007143674 A2 | 12/2007 |
| WO | 2008/058755 A1 | 5/2008 |
| WO | 2008058755 A1 | 5/2008 |
| WO | 2008-095284 | 8/2008 |
| WO | 2008/095284 A1 | 8/2008 |
| WO | 2011/109340 | 9/2011 |
| WO | 2011/109340 A1 | 9/2011 |
| WO | 2011109340 A1 | 9/2011 |
| WO | 2013-059629 | 4/2013 |
| WO | 2013/059629 | 4/2013 |
| WO | 2013/059629 A1 | 4/2013 |
| WO | 2013059629 | 4/2013 |
| WO | 2014/007972 | 1/2014 |
| WO | 2014/153559 | 9/2014 |
| WO | 2020/081952 A1 | 4/2020 |

OTHER PUBLICATIONS

Schianti et al, Title: Rifampicin Nanoprecipitation using Flow Focusing Microfluidic Device; J Nanomed Nanotechol, vol. 4, issue 4, published Apr. 25, 2013. (Year: 2013).*

Kemp SF, Lockey RF, Simons FE. Epinephrine: the drug of choice for anaphylaxis. A statement of the World Allergy Organization. Allergy 2008; 63:1061-70.

McLean-Tooke AP, Bethune CA, Fay AC, Spickett GP. Adrenaline in the treatment of anaphylaxis: what is the evidence? BMJ 2003; 327:1332-5.

Simons KJ, Simons FE. Epinephrine and its use in anaphylaxis: current issues. Curr Opin Allergy Clin Immunol 2010; 10:354-61.

Soar J, Pumphrey R, Cant A, Clarke S, Corbett A, Dawson P, et al. Emergency treatment of anaphylactic reactions—guidelines for healthcare providers. Resuscitation 2008; 77:157-69.

Simons FE. Epinephrine auto-injectors: first-aid treatment still out of reach for many at risk of anaphylaxis in the community. Ann Allergy Asthma Immunol 2009; 102:403-9.

Simons FER. Lack of worldwide availability of epinephrine autoinjectors for outpatients at risk of anaphylaxis. Ann Allergy Asthma Immunol 2005; 94:534-8.

Bredenberg S, Duberg M, Lennernas B, Lennernas H, Pettersson A, Westerberg M et al. In vitro and in vivo evaluation of a new sublingual tablet system for rapid oromucosal absorption using fentanyl citrate as active substance. Eur J Pharm Sci 2003; 20:327-34.

Glover ED, Glover PN, Franzon M, Sullivan CR, Cerullo CC, Howell RM, et al. A comparison of a nicotine sublingual tablet and placebo for smoking cessation. Nicotine Tob Res 2002; 4:441-50.

Guez S. Efficacy of desensitization via the sublingual route in mite allergy. Chem Immunol Allergy 2003; 82:62-76.

Rawas-Qalaji MM, Simons FE, Simons KJ. Sublingual epinephrine tablets versus intramuscular injection of epinephrine: Dose equivalence for potential treatment of anaphylaxis. J Allergy Clin Immunol 2006; 117:398-403.

Rawas-Qalaji MM, Simons FE, Simons KJ. Epinephrine for the treatment of anaphylaxis: do all 40 mg sublingual epinephrine tablet formulations with similar in vitro characteristics have the same bioavailability? Biopharm Drug Dispos 2006; 27:427-35.

Saxena P, Salhan S, Sarda N. Sublingual versus vaginal route of misoprostol for cervical 20 ripening prior to surgical termination of first trimester abortions. Eur J Obstet Gynecol Reprod Biol, 125:109-113, 2006.

Chapter 8, Neurotransmission: The Autonomic and Somatic Motor Nervous Systems in Goodman & Gilman's the Pharmacological Basis of Therapeutics. 12 ed., 16 pages, 2011.

Rachid O, Simons FE, Rawas-Qalaji M, Simons KJ. An electronic tongue: evaluation of the masking efficacy of sweetening and/or flavoring agents on the bitter taste of epinephrine. AAPS PharmSciTech 2010; 11:550-7.

Rawas-Qalaji MM, Simons FE, Simons KJ. Fast-disintegrating sublingual epinephrine 30 tablets: effect of tablet dimensions on tablet characteristics. Drug Dev Ind Pharm 2007; 33:523-30.

Rawas-Qalaji MM, Simons FER, Simons KJ. Fast-Disintegrating Sublingual Tablets: Effect of Epinephrine Load on Tablet Characteristics. AAPS PharmSciTech 2006; 7: Article 41.

Muller RH, Gohla S, Keck CM. State of the art of nanocrystals â€" Special features, production, nanotoxicology aspects and intracellular delivery. European Journal of Pharmaceutics and Biopharmaceutics; 78:1-9.

USP/NF. Physical Tests: Uniformity of Dosage Units (905). 31/26 ed. Rockville, MD: United States Pharmacopeial Convention, Inc.; 2008.

USP/NF. Official Monograph: Epinephrine Injection. 31/26 ed. Rockville, MD: United States Pharmacopeial Convention, Inc.; 2008.

USP/NF. Physical Tests: Tablet Friability (1216). 31/26 ed. Rockville, MD: United States Pharmacopeial Convention, Inc.; 2008.

Olfert ED, Cross BM, McWilliam AA. Guide to the care and use of experimental animals. 2 ed. Ottawa: Canadian Council on Animal Care; 1993.

Hjemdahl P. Inter-laboratory comparison of plasma catecholamine determinations using several different assays. Acta Physiol Scand Suppl 1984; 527:43-54.

Hjemdahl P. Catecholamine measurements in plasma by high-performance liquid chromatography with electrochemical detection. Methods Enzymol 1987; 142:521-34.

Ganhao MF, Hattingh J, Hurwitz ML, Pitts NI. Evaluation of a simple plasma catecholamine extraction procedure prior to high-performance liquid chromatography and electrochemical detection. J Chromatogr 1991; 564:55-66.

Rachid O, Rawas-Qalaji M, Simons FE, Simons KJ. Rapidly-disintegrating sublingual tablets of epinephrine: role of non-medicinal ingredients in formulation development. Eur J Pharm Biopharm 2012; 82:598-604.

Rachid O, Rawas-Qalaji MM, Simons FE, Simons KJ. Epinephrine (adrenaline) absorption from new-generation, taste-masked sublingual tablets: a preclinical study. J Allergy Clin Immunol 2013; 131:236-8.

Liu Y, Sun C, Hao Y, Jiang T, Zheng L, Wang S. Mechanism of dissolution enhancement and bioavailability of poorly water soluble celecoxib by preparing stable amorphous nanoparticles. J Pharm Pharm Sci 2010; 13:589-606.

(56) References Cited

OTHER PUBLICATIONS

Ma Q, Sun H, Che E, Zheng X, Jiang T, Sun C, et al. Uniform nano-sized valsartan for dissolution and bioavailability enhancement: Influence of particle size and crystalline state. Int J Pharm 2013; 441:75-81.
Dali MM, Moench PA, Mathias NR, Stetsko PI, Heran CL, Smith RL. A rabbit model for sublingual drug delivery: comparison with human pharmacokinetic studies of propranolol, verapamil and captopril. J Pharm Sci 2006; 95:37-44.
Ong CM, Heard CM. Permeation of quinine across sublingual mucosa, in vitro. Int J Pharm 2009; 366:58-64.
For Canadian Patent Application No. 2,853,084: Office Action dated Oct. 25, 2018 (3 pages).
International Search Report dated Aug. 20, 2014, Written Opinion dated Aug. 20, 2014 and International Preliminary Examination Report dated Sep. 22, 2015 for PCT/US14/31579.
Office Action dated Mar. 16, 2018 for U.S. Appl. No. 15/358,743.
Response filed May 16, 2018 for U.S. Appl. No. 15/358,743.
Office Action dated Sep. 25, 2018 for U.S. Appl. No. 15/358,743.
Response filed Sep. 19, 2018 with European Patent Office for EP patent application No. 14 768 584.6.
International Search Report dated Dec. 22, 2006, Written Opinion dated Dec. 22, 2006 and International Prelim Report on Patentability dated Dec. 10, 2007, for PCT/CA06/001472.
International Search Report dated Apr. 29, 2008, Written Opinion dated Apr. 29, 2008 and International Prelim Report on Patentability dated Apr. 11, 2009, for PCT/CA08/00197.
Office action dated Mar. 16, 2009 for U.S. Appl. No. 11/672,503, 8 pages.
Written Opinion dated Jan. 11, 2013 and International Prelim Report on Patentability dated Apr. 22, 2014, for PCT/US2012/061074.
International Search Report dated Jan. 11, 2013 for PCT/US2012/061074.
International Prelim Report on Patentability dated Sep. 4, 2012 for PCT/US2011/26604.
Office action dated Mar. 13, 2009 for U.S. Appl. No. 11/530,360.
For U.S. Appl. No. 13/582,346 office actions dated Sep. 12, 2013; dated Feb. 7, 2014 response dated Dec. 12, 2013.
International Search Report and Written Opinion dated Aug. 20, 2014 for PCT/US14/31579.
Office Action for U.S. Appl. No. 15/882,399 dated Mar. 29, 2019.
Birudaraj et al., 2004, J Pharm Sci 94.
Ishikawa et al., 2001, Chem Pharm Bull 49: 230-23.
Price et al., 1997, Obstet Gynecol 89: 340-345.
Kroboth et al., 1995, J Clin Psychopharmacol 15: 259-262.
Cunningham et al., 1994, J Clin Anesth 6: 430-433.
Scavone et al., 1992, Eur J Clin Pharmacol 42: 439-443.
Spenard et al., 1988, Biopharm Drug Dispos 9: 457-464.
Mitra et al., 2002, Encyclopedia of Pharm. Tech., 2081-2095.
Joint Task Force on Practice Parameters, 2005, J Allergy Clin Immunol 115: S483-S523.
Lieberman, 2003, Curr Opin Allergy Clin Immunol 3: 313-318.
Simons, 2004, J Allergy Clin Immunol 113: 837-844, First-Aid Treatment of Anaphylaxis to Food, 8 pgs.
Simons, F.E.R. J Allergy Clin Immunol 124(4):625-636 2009, Anaphylaxis: Recent Advances in Assessment and Treatment, 12 pgs.
Simons, F.E.R. J Allergy Clin Immunol 125:S161-181 2010, Anaphylaxis, 21 pgs.
Simons, K.J. et al. Current Opinion in Clinical Immunology 10:354-361 2010, Epinephrine and Its use in Anaphylaxis, 8 pgs.
Connors et al., 1986, in Chemical Stability of Pharmaceuticals: A Handbook for Pharmacists, Wiley-Interscience Publication: New York.
Gu et al., 2002, Biopharm Drug Dispos 23: 213-216.
Simons et al., 2004, J Allergy Clin Immunol 113: 425-438, S260 Abstract.
Rawas-Qalaji et al. J Allergy Clin Immunol 117:398-403 2006.
Rawas-Qalaji et al. Biopharm Drug Disposition 27 (9):427-435 2006.
AAPS PharmSciTech 12:544-552,2011.
Rachid, O. et al. AAPS PharmSciTech 12(2):544-552 2011.
USP/NF. Physical Tests: Dissolution (711); 22/17 ed. Rockville, MD: United States Pharmaceutical Convention Inc; 2007.
Rachid, O. et al. AAPS PharmSciTech 11(2):550-557 2010.
Rawas-Qalaji, AAPS PharmSciTech. 2006;7(2): Article 41.
Motwani et al., 1991, Clin Pharmacokinet 21: 83-94.
Written Opinion dated Apr. 29, 2011 for PCT/US11/26604 filed Mar. 1, 2010.
International Search Report dated Apr. 29, 2011 for PCT/US11/26604 filed Mar. 1, 2010.
Written Opinion dated Jan. 11, 2013 for PCT/US12/061074 filed Oct. 19, 2012.
International Search Report dated Jan. 11, 2013 for PCT/US12/061074 filed Oct. 19, 2012.
Response filed Apr. 24, 2019 for Canadian Patent Application No. 2,853,084.
European Search Report for EP12842206 dated Mar. 31, 2015, 7 pages (national stage of PCT/US2012/61074 published as WO2013/59629).
Ting Qiao et al, Conjugation of catecholamines on magnetic nanoparticles coated with sulfonated chitosan, Colloids and Surfaces A: Physicochem, Eng. Aspects 380 (2011) 169-174.
Simons, Is epinephrine administralion by sublingual table feasible for the first-aid treatment of anaphylaxes?, Biopharm Drup Dispos, Jul. 23, 2002 (5): 213-6, abstract.
International Preliminary Report on Patentability and Written Opinion for PCT/US13/45836 filed Jun. 14, 2013.
PubcheM: title: chemical and physical properties of epinephrine (only pertinent pp. of 1 and 8), downloaded on Jun. 6, 2016, from http:/dav.uspto.gove/webappapplicationViewer.html?casenumber_14778887#).
Spyros Papiris, et al, Clinical Review: Severe Asthma, Critical Care. vol. 6(1), p. 30-44, published online Nov. 22, 2001.
Final Office Action dated Apr. 30, 2019, for U.S. Appl. No. 15/358,743 45 pages.
Response filed May 2, 2019, to Office Action from European Patent Office for EP Patent Application No. 14 768 584.6, 11 pages.
For EP Application 14 768 584.6 (regional stage of PCT/US2014/31579): claim amendments dated May 12, 2016; second examiner's report dated May 28, 2018 (10 pages).
For EP Application 14 768 584.6 (regional stage of PCT/US2014/31579): European Search Report dated Aug. 10, 2016 (8 pages).
International Preliminary Report and Written Opinion dated May 1, 2014 for PCT/US2013/045836.
For U.S. Appl. No. 15/882,399: Office Action dated Mar. 22, 2018; Response dated Jun. 22, 2018 (24 pages).
Office Action for U.S. Appl. No. 15/358,743 dated Sep. 25, 2018.
Response for U.S. Appl. No. 15/358,743, filed Jan. 25, 2019.
Final Office Action for U.S. Appl. No. 15/882,399 dated Sep. 27, 2019.
RCE Response for U.S. Appl. No. 15/882,399, filed Jan. 28, 2019.
Final Office Action for U.S. Appl. No. 15/262,961 dated Jul. 24, 2018.
Response for U.S. Appl. No. 15/262,961, filed Oct. 9, 2018.
International Search Report dated Jan. 16, 2014 for PCT/US2013/045836.
Written opinion dated Jan. 16, 2014 for PCT/US2013/045836.
Rawan-Qalaji et all, Development of Epinephrine Nanoparticles Using Chitosan for the Treatment of Anaphylaxis, Poster presentation at the 2011 AAPS Annual Meeting and Exposition, Oct. 23-27, 2011, Washington DC, Poster No. W4174.
Adrenaline into Melanin, Br Med J, May 29, 2971, 2(5760): 486.
Sigma-Aldrich, Material Safety Data Sheet, Version 3.2, printed May 1, 2012 (6 pages).
Saxena, Sublingual versus vaginal route of misoprostol for cervical ripening prior to surgical termination of first timrester abortions, Eur J Obstet Gynecol Reprod Biol Mar. 1, 2006, 125(1): 109-13, abstract.
Office Action dated Nov. 17, 2015 for EP 14-768584 (national stage of PCT/US2014/31579).

(56) References Cited

OTHER PUBLICATIONS

Abdelbary, G. et al., "Determination of the in vitro disintegration profile of rapidly disintegrating tablets and correlation with oral disintegration," Int. J. Pharm. 292:29-41 (2005).

Allen, L., "Rapid-Dissolve Technology: An Interview with Lloyd V. Allen, Jr. PhD, RPh," Int. J. of Pharma. Compounding 7:449-450 (2003).

Aly, A. et al., "Superdisintegrantsfor Solid Dispersion to Produce Rapidly Disintegrating TenoxicamTablets via Camphor Sublimation," Pharma. Tech.7:68-78 (2005).

Aurora, J. and Pathak, V., "Oral Disintegrating Dosage Forms: An Overview," Drug Deliv. Technol. 5:50-54 (2005).

Bi, Y.X. et al., Evaluation of Rapidly Disintegrating Tablets Prepared by a Direct Compression Method, Drug Dev. Ind. Pharm. 25:571-581 (1999).

Bi, Y. et al., "Preparation and Evaluation of a Compressed Tablet Rapidly Disintegrating in the Oral Cavity," Chem. Pharm. Bull. 44:2121-2127 (1996).

Birudaraj, R. et al., "Buccal Permeation of Buspirone: Mechanistic Studies on Transport Pathways," J. Pharm. Sci. 94:70-78 (2004).

Chang, R. et al., "Fast-Dissolving Tablets," Pharm. Tech. 24:52-58 (2000).

Cunningham, F. et al., "Comparative Phatinacokinetics of Oral versus Sublingual Clonidine," J. Clin. Anesth. 6:430-433 (1994).

De Vries, M. et al., "Developments in Buccal Drug Delivery," Crit. Rev. Ther. Drug Carr. Syst. 8:271-303 (1991).

Dobetti, L., "Fast-Melting Tablets: Developments and Technologies," Pharmaceutical Technology Europe 12:32-42 (2000).

Dor, P. and Fix, J., "In Vitro Determination of DisintegrationTime of Quick-Dissolve Tablets Using a New Method," Pharm. Dev. Technol. 5:575-577 (2000).

El-Arini, S. and Clas, S., "Evaluation of Disintegration Testing of Different Fast Dissolving Tablets Using the Texture Analyzer," Pharm. Dev. Technol. 7:361-371 (2002).

Fell, J.T. and Newton, J.M., "Determnation ofTablet Strength by the Diametral-Compression Test," J. Pharm. Sci. 59:688-691 (1970).

Ganhao, M. et al., "Evaluation of a simple plasma catecholamine extraction procedure prior to high-performance liquid chromatography and electrochemical detection," J. Chromatogr, 564:55-66 (1991).

Gu, X. et al., "Is Epinephrine Administration by Sublingual Tablet Feasible for the First-Aid Treatment of Anaphylaxis? A Proof-Of-Concept Study," Biopharm. Drug Dispos. 23:213-216 (2002).

Gu, X., et al., "Epinephrine Absorption after Different Routes of Administration in an Animal Model," Biopharm Drug Dispos. 20: 401-405 (1999).

Hamilton, E. et al., "Advanced Orally Disintegrating Tablets Bring Significant Benefits to Patients & Product Life Cycles," Drug Deliv. Technol. 5:34-37 (2005).

Hedenus, P. et al., "Characterisation of instantaneous water absorption properties of pharmaceutical excipients," Int. J. Pharm. 141:141-149 (2000).

Hjemdahl, P., "Catecholamine Measurements in Plasma by High-Performance Liquid Chromatography with Electrochemical Detection," Methods in Enzymol. 142:521-534 (1987).

Hjemdahl, P., "Inter-laboratory comparison of plasma catecholamine determinations using several different assays," Acta Physiol. Scand. Suppl. 527:43-54 (1984).

*Human Physiology: From Cells to Systems*, Sherwood I.., (ed.) Brooks/Cole/Thomson Learning: Belmont, CA, 2004; Chapter 16, pp. 591-645.

Ishikawa, T. et al., "Pharmacokinetics of Acatominophen from Rapidly Disintegrating Compressed Tablet Prepared Using Microcrystalline Cellulose (PH-M-06) and Spherical Sugar Granules," Chem. Pharm. Bull. 49:230-232 (2001).

Ishikawa, T. et al., "Preparation of Rapidly Disintegrating Tablet Using New Types of Microcrystalline Cellulose (PH-M Series) and Low Substituted-Hydroxypropylcellulose or Spherical Sugar Granules by Direct Compression Mehod," Chem. Pharm. Bull. 49:134-139 (2001).

Kroboth, P. et al., "Triazopam Pharmacokinetics After Intravenous, Oral, and Sublingual Administration," J. Clin. Psychopharmacol. 15:259-262 (1995).

Lieberman, P. et al., "Joint Task Force on Practice Parameters," J. Allergy Clin. Immunol. 115:S483-S523 (2005).

Lieberman, P., "Use of epinephrine in the treatment of anaphylaxis," Curr. Opin. Allergy Clin. Immunol. 3:313-318 (2003).

Mitra, A. et al., "Peptides and Proteins—Buccal Absorption," Encyclopedia of Pharm. Tech., pp. 2081-2095 (2002).

Motwani, J. and Lipworth, B., "Clinical Pharmacokinetics of Drugs Administered Buccally and Sublingually," Clin. Pharmacokinet. 21:83-94 (1991).

Parakh, S.R. and Gothoskar, A.V., "A Review of Mouth Dissolving Tablet Technologies," Pharm. Tech. 27:92-100 (2003).

Price, T.M. et al., "Single-Dose Pharmacokinetics of Sublingual Versus Oral Administration of Micronized 17β-Estradiol," Obstet. Gynecol. 89:340-345 (1997).

Rawas-Qalaji, M. et al., "Fast-Disintegrating Sublingual Bpinephrine Tablets: Effect of Drug and Tablet Dimensions on Tablet Characteristics," AAPS 7(52):Abstract W5220 (2005).

Rawas-Qalaji, M. et al., "Sublingual epinephrine tablets versus intramuscular injection of epinephrine; Dose equivalence for potential treatment of anaphylaxis," J. Allergy Clin. Immunol. 117(2):398-403 (Feb. 2006).

Rawas-Qalaji, M. et al., "Fast-Disintegrating Sublingual Epinephrine Tablets: Effect of Epinhephrine Load on Tablet Characteristics," AAPS PharmSciTech 7(2) Article 41: E1-E7 (2006).

Rawas-Qalaji, M. et al., "Fast-Disintegrating Sublingual Epinephrine Tablets: Long Term Stability Study," AAPS 7(52) Abstract W5219 (2005).

Rawas-Qalaji, M. et al., "Formulation of Fast-Disintegrating Sublingual Epinephrine Tablets for the First-Aid Treatment of Anaphylaxis Away From Health Care Facilities," AAPS 6(4) Abstract W4178 (2004).

Rawas-Qalaji, M. et al., "Evaluation of the Effect of Changing Tablet Dimensions on the Characteristics of Fast-disintegrating Sublingual Epinephrine Tablets for the First-Aid Treatment of Anaphylaxis Away From Health Care Facilites," AAPS 6(4) Abstract 4179 (2004).

Rawas-Qalaji, M. et al., "Epinephrine for the Treatment of Anaphylaxis: Do All 40mg Sublingual Epinephrine Tablet Formulations with Similar In Vitro Characteristics Have the Same Bioavailability?" Biopharm. Drug Dispos. 27:427-435 (2006).

Sastry, S. et al., *Drug Del. to the Oral Cavity: Molecule to Market*, Chapter 13, pp. 311-316 (2005), eds. Taylor & Francis , CRC Press.

Sastry, S. et al., "Recent technological advances in oral drug delivery—a review," Pharm Sci. Technol. Today 3:138-145 (2000).

Scavone, J.M. et al., "The pharmacokinetics and pharmacodynamics of sublingual and oral alprazolam in the post-prandial state," Eur. J. Clin. Pharmacol. 42:439-443 (1992).

Schiermeier, S. and Schmidt, P., "Fast dispersable ibuprofen tablets," Eur. J. Pharm. Sci. 15:295-305 (2002).

Sharma, N. et al., "Manufacturing Technology Choices for Mouth Dissolving Tablets," Pharma. Tech. North America 10-15 (2003).

Simons, F. Estelle, "First-aid treatment of anaphylaxis to food: Focus on epinephrine," J. Allergy Clin. Immunol. 113:837-844 (2004).

Simons, K.J. et al., "Sublingual epinephrine administration in humans: A preliminary study," J. Allergy Clin. Immunol. 113 (Suppl. 1):S260 (2004).

Simons, F. Estelle, "EpiPen Jr versus EpiPen in young children weighing 15 to 30 kg at risk for anaphylaxis," J. Allergy Clin. Immunol. 109(1):171-175 (2002).

Simons, F. Estelle et al., "Outdated EpiPen and EpiPen Jr. autoinjectors: Past their Prime?" J. Allergy Clin. Immunol. 105:1025-1030 (2000).

Spenard, J. et al., "Placebo-Controlled Comparative Study of the Anxiolytic Activity and of the Pharmacokinetics of Oral and Sublingual Lorazepam in Generalized Anxiety," Biopharm. Drug Dispos. 9:457-464 (1988).

Sugimoto, M. et al., "The Preparation of Rapidly Disintegrating Tablets in the Mouth," Pharm. Dev. Technol. 6:487-493 (2001).

(56) References Cited

OTHER PUBLICATIONS

Verma, R. and Garg, S., "Current Status of Drug Delivery Technologies and Future Directions," Pharma. Technol. On-Line 25:1-4 (2001).
Watenabe, Y. et al., "New Compressed Tablet Rapidly Disintegrating in Saliva in the Mouth Using Crystalline Cellulose and a Disintegrant," Biol. Pharm. Bull. 18:1308-1310 (1995).
Final Office Action for U.S. Appl. No. 15/882,399 dated Sep. 27, 2018.
Response to Final Office Action for U.S. Appl. No. 15/358,743, filed Aug. 30, 2019.
European Search Report for EP Patent Application No. 13812628.9 dated Jul. 25, 2019.
Office Action for U.S. Appl. No. 15/358,743 dated Sep. 18, 2019.
Response to Final Office Action for U.S. Appl. No. 15/358,743, filed Jan. 16, 2020.
Response to Final Office Action for U.S. Appl. No. 16/377,810, filed Feb. 10, 2020.
Office Action for EP Patent Application No. 14 768 584.6, dated Sep. 26, 2019.
Merriam Webster Definition of "Microcrystal" dated Sep. 26, 2019.
Collins Dictionary Definition of "Microparticle" retrieved Sep. 26, 2019.
Office Action for U.S. Appl. No. 16/377,810, dated Oct. 9, 2019.
Office Action for Canadian Patent Application No. 2,853,084: dated Sep. 12, 2019.
Response to Office Action for U.S. Appl. No. 15/882,399, filed Jul. 26, 2019.
Office Action for U.S. Appl. No. 16/377,810 dated May 13, 2020.
For Canadian Patent Application No. 2,853,084, filed Oct. 19, 2012: Office Action dated Jun. 8, 2020 Response filed Oct. 6, 2020.
Office action for Canadian Patent App. No. 2853084 dated Feb. 9, 2021.
Office action for Canadian Patent Application No. 2,907,770 dated Feb. 9, 2021.
Response for EP Patent Application No. 14 768 584.6, filed Jul. 6, 2020.
Examination Report for European Patent Application No. 12842206.0, dated Apr. 9, 2020.
Response filed Nov. 6, 2020 for U.S. Appl. No. 16/377,810.
Office Action for Canadian Patent Application No. 2,876,883, dated Nov. 19, 2020.
For Canadian Patent Application No. 2,907,770, filed Mar. 24, 2014: Office Action dated Apr. 15, 2020 Response for filed Oct. 15, 2020.
Office action for European Patent Application No. 13812628.9, dated Apr. 22, 2021.
For U.S. Appl. No. 16/377,810: Final Office Action dated Mar. 1, 2021.
For Canadian Patent Application No. 2,876,883: Response dated Nov. 22, 2019; Office Action dated Feb. 25, 2020; Response dated Aug. 25, 2020; Office Action dated Nov. 19, 2020; Response filed Mar. 18, 2021.
For Canadian Patent Application No. 2,907,770, filed Mar. 24, 2014: Office Action dated Feb. 9, 2021.
For EP Application 14 768 584.6 (regional stage of PCT/US2014/31579): response dated Sep. 19, 2018; office action dated Jan. 15, 2019; response dated May 2, 2109; office action dated Sep. 26, 2019; response dated Dec. 18, 2019; Office Action dated May 8, 2020; response filed Jul. 6, 2020.
For Canadian Patent Application No. 2,853,084: Response filed Mar. 12, 2020.
International Search Report and Written Opinion for PCT/2019/056967 dated Dec. 23, 2019.
International Preliminary Report on Patentability and Written Opinion for PCT/2019/056967 dated Apr. 29, 2021.
RCE response filed Jul. 1, 2021, for U.S. Appl. No. 16/377,810.
For Canadian Patent Application No. 2,853,084: Response filed Jun. 9, 2021.
For Canadian Patent Application No. 2,907,770, filed Mar. 24, 2014: Response for filed Jun. 9, 2021.

\* cited by examiner

COMPOSITIONS INCLUDING EPINEPHRINE MICROCRYSTALS

FIELD OF THE INVENTION

The invention generally relates to compositions and methods for treatment of conditions responsive to epinephrine (also known as adrenaline), particularly to compositions and methods for emergency treatment of conditions responsive to epinephrine, and most particularly to compositions including epinephrine fine particles, including epinephrine nanoparticles or nanocrystals and epinephrine microparticles or microcrystals, for sublingual administration in treatment of conditions responsive to epinephrine.

BACKGROUND

Tablets that disintegrate or dissolve rapidly in the patient's mouth without the use of water are convenient for the elderly, young children, patients with swallowing difficulties, and in situations where water is not available. For these specially designed formulations, the small volume of saliva that is available is sufficient to disintegrate or dissolve a tablet in the oral cavity. The drug released from these tablets can be absorbed partially or entirely into the systemic circulation from the buccal mucosa or sublingual cavity, or can be swallowed as a solution to be absorbed from the gastrointestinal tract.

The sublingual route usually produces a faster onset of action than traditional orally-administered tablets and the portion absorbed through the sublingual blood vessels bypasses the hepatic first pass metabolic processes (Birudaraj et al., 2004, *J Pharm Sci* 94; Motwani et al., 1991, *Clin Pharmacokinet* 21: 83-94; Ishikawa et al., 2001, *Chem Pharm Bull* 49: 230-232; Price et al., 1997, *Obstet Gynecol* 89: 340-345; Kroboth et al., 1995, *J Clin Psychopharmacol* 15: 259-262; Cunningham et al., 1994, *J Clin Anesth* 6: 430-433; Scavone et al., 1992, *Eur Clin Pharmacol* 42: 439-443; Spenard et al., 1988, *Biopharm Drug Dispos* 9: 457-464).

Likewise, due to high buccal and sublingual vascularity, buccally- or sublingually-delivered drugs can gain direct access to the systemic circulation and are not subject to first-pass hepatic metabolism. In addition, therapeutic agents administered via the buccal or sublingual route are not exposed to the acidic environment of the gastrointestinal tract (Mitra et al., 2002, *Encyclopedia of Pharm. Tech.*, 2081-2095). Further, the buccal and sublingual mucosas have low enzymatic activity relative to the nasal and rectal routes. Thus, the potential for drug inactivation due to biochemical degradation is less rapid and extensive than other administration routes (de Varies et al., 1991, *Crit. Rev. Ther. Drug Carr. Syst.* 8: 271-303).

The buccal and sublingual mucosas are also highly accessible, which allows for the use of tablets which are painless, easily administered, easily removed, and easily targeted. Because the oral cavity consists of a pair of buccal mucosa, tablets, such as fast disintegrating tablets, can be applied at various sites either on the same mucosa or, alternatively, on the left or right buccal mucosa (Mitra et al., 2002, *Encyclopedia of Pharm. Tech.*, 2081-2095). In addition, the buccal and sublingual routes could be useful for drug administration to unconscious patients, patients undergoing an anaphylactic attack, or patients who sense the onset of an anaphylactic attack.

Anaphylaxis is a sudden, severe systemic allergic reaction, which can be fatal within minutes. Epinephrine (Epi) is the drug of choice for the treatment of anaphylaxis worldwide (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844). It is available as an injectable dosage form in ampoules or in autoinjectors, however these are underused when anaphylaxis occurs (Simons, F. E. R. J Allergy *Clin Immunol* 124(4):625-636 2009; Simons, F. E. R. *J Allergy Clin Immunol* 125:S161-181 2010). The drawbacks of Epi auto-injectors include high cost, perceived large size and bulkiness, limitations on repeated dosing (if required), fear and anxiety associated with the use of needles (especially in children), and dosing errors caused by incorrect techniques of administration (Simons, K. J. et al. *Current Opinion in Clinical Immunology* 10:354-361 2010). Furthermore, in aqueous solutions, epinephrine is unstable in the presence of light, oxygen, heat, and neutral or alkaline pH values (Connors et al., 1986, in *Chemical Stability of Pharmaceuticals: A Handbook for Pharmacists*, Wiley-Interscience Publication: New York) and thus has limited shelf-life; approximately one year.

The sublingual route of administration is a promising alternative route for epinephrine administration. The formulation of sublingual tablets of epinephrine would enable the development of tablets with a range of epinephrine doses to match the population on an mg/kg basis. Sublingual tablets of epinephrine would be easy to carry and self-administer eliminating the fear and anxiety associated with needles used in autoinjectors for young children, as well as readily providing the capability of multiple doses. Feasibility studies in humans and animals have shown that epinephrine can be absorbed sublingually (Gu et al., 2002, *Biopharm Drug Dispos* 23: 213-216; Simons et al., 2004, *J Allergy Clin Immunol* 113: 425-438). The recommended dose of epinephrine for the treatment of anaphylaxis is about 0.01 mg/Kg: usually about 0.2 mL to about 0.5 mL of a 1:1000 dilution of epinephrine in a suitable carrier. Based on historical and anecdotal evidence, an approximately 0.3 mg dose of epinephrine, by subcutaneous (SC) or intramuscular (IM) injection into the deltoid muscle, has been agreed upon as the dose required for the emergency treatment of anaphylaxis. Recent studies have demonstrated that if the approximately 0.3 mg dose is administered IM into the laterus vascularis (thigh) muscle, Epi plasma concentrations are higher and occur more quickly than SC or IM administration into the deltoid muscle. (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844)).

As stated above, epinephrine (Epi) is typically administered either subcutaneously (SC) or intramuscularly (IM) by injection. Thus, Epi injections are the accepted first aid means of delivering Epi and are administered either manually or by automatic injectors. It is recommended that persons at risk of anaphylaxis, and persons responsible for children at risk for anaphylaxis, maintain one or more automatic Epi injectors in a convenient place at all times.

Given the difficulties associated with manual subcutaneous (SC) or intramuscular (IM) administration of Epi, such as patient apprehension related to injections or the burden of an at risk person having to always maintain an Epi injector close at hand, there exists a need in the art for more convenient dosage forms which can provide immediate administration of Epi, particularly to a person undergoing anaphylaxis wherein the need for injection or Epi injectors is obviated.

Recently, a novel fast-disintegrating tablet suitable for sublingual (SL) administration of Epi was developed. See related U.S. applications: U.S. Provisional Patent Application No. 60/715,180; U.S. Provisional Patent Application No. 60/759,039; U.S. Utility patent application Ser. No. 11/672,503; and U.S. Utility patent application Ser. No. 11/530,360. Sublingual administration of 40 mg epinephrine as the bitartrate salt using these novel tablets resulted in a rate and an extent of epinephrine absorption similar to that achieved following intramuscular injections of 0.3 mg epinephrine in the thigh. Sublingual doses ranging from 5 to 40 mg epinephrine as the bitartrate salt were studied to achieve equivalent plasma concentrations. In an animal model, it was determined that a 40 mg epinephrine dose administered sublingually as a bitartrate salt in tablet form resulted in plasma epinephrine concentrations similar to those achieved by 0.3 mg epinephrine intramuscular (IM) injection (Rawas-Qalaji et al. *J Allergy Clin Immunol* 117:398-403 2006).

Without being bound by theory, it is thought that fabrication of epinephrine into fine particles, including epinephrine nanoparticles or nanocrystals and epinephrine microparticles or microcrystals, and incorporation of the epinephrine fine particles into a tablet formulation with pharmaceutically-acceptable carriers, penetration enhancers, and mucoadhesives will significantly increase the absorption of SL-administered epinephrine and will result in the reduction of SL epinephrine dose required.

SUMMARY OF THE INVENTION

Epinephrine (Epi) is life-saving in the treatment of anaphylaxis. In community settings, a first-aid dose of epinephrine in an amount of 0.15 mg or 0.3 mg is injected into the mid-outer thigh by patients or caregivers using an auto-injector such as an EpiPen® (epinephrine auto-injector 0.3 or 0.15 mg, Mylan Inc., Basking Ridge, N.J.). Epi auto-injectors are under-used because of needle phobia, bulky size, and high cost; additionally, there are only two fixed doses, shelf-life is only 12-18 months, and unintentional injection and injury sometimes occur.

The instant invention circumvents the aforementioned problems by providing a fast-disintegrating epinephrine tablet formulation for anaphylaxis treatment. Although this formulation was designed with regard to anaphylaxis, it is equally effective and contemplated for use in treatment of any condition responsive to epinephrine such as cardiac events, i.e. cardiac arrest, and breathing difficulties, i.e. asthma, bronchial asthma, bronchitis, emphysema, and respiratory infections.

In a validated rabbit model, this fast-disintegrating epinephrine tablet formulation resulted in plasma epinephrine concentrations similar to those achieved after a 0.3 mg epinephrine intra-muscular injection (Rawas-Qalaji et al. *J Allergy Clin Immunol* 117:398-403 2006). Furthermore, epinephrine was stable in these fast-disintegrating tablets for at least seven years.

One of the most common approaches to enhance the rate of drug dissolution and absorption is to significantly reduce its particle size to the micro- or nano-size range. Drug nanocrystals (NC) or microcrystals (MC) are advantageous due to the minimal required excipients and almost 100% of the pure drug is produced during the fabrication process[17]. Also, the collected dried drug NC or MC can be formulated into various dosage forms.

The phrase "epinephrine fine particles" refers to epinephrine particles of about 2.5 μm or less to about 100 nm in size and includes epinephrine nanoparticles or nanocrystals and epinephrine microparticles or microcrystals.

In one aspect, the invention provides epinephrine fine particles.

In one aspect, the invention provides epinephrine nanoparticles. The epinephrine can be either an epinephrine base or an epinephrine bitartrate salt.

In another aspect, the invention provides epinephrine nanocrystals. A nanocrystal is a nanoparticle having a crystalline structure. The term "nanocrystal" is a more specific term for describing a nanoparticle. A drug nanocrystal contains almost 100% pure drug, thus an epinephrine nanocrystal contains almost 100% pure epinephrine. A drug nanoparticle can include nanocrystals or a drug encapsulated within a polymer at different ratios. One example is the epinephrine nanoparticles comprising chitosan and tripolyphosphate (TPP) described in the previously-filed related application; U.S. Provisional Patent Application Ser. No. 61/550,359, filed on Oct. 21, 2011.

In another aspect, the invention provides a composition including epinephrine nanoparticles or nanocrystals capable of enhancing the sublingual bioavailability of epinephrine for the emergency treatment of anaphylaxis.

In another aspect, the invention provides "oral disintegrating tablets (ODTs)" including epinephrine nanoparticles or nanocrystals or epinephrine microparticles or microcrystals.

As described herein, buccal or sublingual oral disintegrating tablets (ODTs) are distinguished from conventional sublingual tablets, lozenges, or buccal tablets by the ODTs' ability to fully dissolve or disintegrate in less than about one minute in the mouth.

The invention also provides pharmaceutical compositions including epinephrine nanoparticles or nanocrystals or epinephrine microparticles or microcrystals in ODT form.

The invention also provides a pharmaceutical composition including epinephrine nanoparticles or nanocrystals or epinephrine microparticles or microcrystals and a pharmaceutically-acceptable carrier for buccal or sublingual administration.

The phrase "pharmaceutically-acceptable carrier" refers to an inactive and non-toxic substance used in association with an active substance, i.e. epinephrine, especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (NMIs).

The invention also provides a pharmaceutical composition, for buccal or sublingual administration, including epinephrine nanoparticles or nanocrystals or epinephrine microparticles or microcrystals and at least one of a pharmaceutically-acceptable carrier, a surfactant, a penetration enhancer, and a mucoadhesive. The pharmaceutical composition can further include at least one of a taste enhancer and a sweetening agent and mouthfeel enhancer. A non-limiting example of a taste enhancer is citric acid. Citric acid masks the bitter taste of epinephrine. A non-limiting example of a sweetening agent and mouthfeel enhancer is mannitol. The pharmaceutical composition can further include at least one of a filler, a lubricant, and a disintegrant. Non-limiting examples include microcrystalline cellulose (filler), magnesium stearate (lubricant), and hydroxypropyl ethers of cellulose (disintegrant).

Additionally, the invention provides a pharmaceutical composition including epinephrine nanoparticles or nanocrystals or epinephrine microparticles or microcrystals, in which the bitter taste of the epinephrine is masked by a taste enhancer. A non-limiting example of a taste enhancer is citric acid.

In another aspect, the invention provides a method for enhancing sublingual bioavailability of epinephrine in a subject in need thereof including steps for providing a composition including epinephrine nanoparticles or nanocrystals or epinephrine microparticles or microcrystals and at least one pharmaceutically-acceptable carrier and administering the composition to the subject. The described fast-disintegrating epinephrine tablets enhance bioavailability of epinephrine by releasing epinephrine within sixty seconds of administration.

In another aspect, the invention provides a method for treating a condition responsive to epinephrine in a subject in need thereof including steps for providing a composition including epinephrine nanoparticles or nanocrystals or epinephrine microparticles or microcrystals and at least one pharmaceutically-acceptable carrier and administering the composition to the subject. Conditions responsive to epinephrine react to administration of epinephrine. Non-limiting examples of conditions responsive to epinephrine include a cardiac event, i.e. cardiac arrest, or an allergic reaction, i.e. anaphylaxis, asthma, or bronchial asthma.

The phrase "effective amount" refers to the amount of a composition necessary to achieve the composition's intended function.

The phrase "pharmaceutically-effective dose" refers to the amount of a composition necessary to achieve a desired pharmaceutical effect. It is often desirable to use the smallest effective dose of a drug. One example of a dose range for the described epinephrine nanoparticles or nanocrystals or epinephrine microparticles or microcrystals is approximately 10 mg to 40 mg epinephrine nanoparticles or nanocrystals or epinephrine microparticles or microcrystals.

The phase "therapeutically-effective amount" refers to the amount of a composition required to achieve the desired function, i.e. treatment of the condition responsive to epinephrine.

In another aspect, the invention provides a method for treating a breathing difficulty in a subject in need thereof including steps for providing a composition including epinephrine nanoparticles or nanocrystals or epinephrine microparticles or microcrystals and at least one pharmaceutically-acceptable carrier and administering the composition to the subject. Breathing difficulties responsive to epinephrine include, but are not limited to, breathing difficulties associated with anaphylaxis, asthma, bronchial asthma, bronchitis, emphysema, and respiratory infections.

The invention additionally provides a method for treatment of an allergic emergency in a subject diagnosed with or suspected of having an allergic emergency including steps for providing a composition including epinephrine nanoparticles or nanocrystals or epinephrine microparticles or microcrystals and at least one pharmaceutically-acceptable carrier and administering the composition to the subject. Non-limiting examples of allergic emergencies are anaphylaxis, asthma, and bronchial asthma.

In an additional aspect, the invention provides a method for treatment of a cardiac event in a subject diagnosed with or suspected of having a cardiac event including steps for providing a composition including epinephrine nanoparticles or nanocrystals or epinephrine microparticles or microcrystals and at least one pharmaceutically-acceptable carrier and administering the composition to the subject. A non-limiting example of a cardiac event is cardiac arrest.

Any of the above-described epinephrine fine particles (including epinephrine nanoparticles or nanocrystals and epinephrine microparticles or microcrystals), compositions, and pharmaceutical compositions can be formulated for buccal or sublingual administration, particularly those epinephrine fine particles (including epinephrine nanoparticles or nanocrystals and epinephrine microparticles or microcrystals), compositions, and pharmaceutical compositions intended for use in emergency situations.

In another aspect, any of the above-described epinephrine fine particles (including epinephrine nanoparticles or nanocrystals and epinephrine microparticles or microcrystals) can be used in the manufacture of any of the above-described compositions and pharmaceutical compositions.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

FIG. 5A is another view of the DSC spectrum of epinephrine bitartrate (EpiBit) before processing. FIG. 5B is another view of the DSC spectrum of epinephrine bitartrate (EpiBit) after processing. FIG. 5C is a Scanning Electron Microscopy (SEM) image of epinephrine bitartrate (EpiBit) before processing. FIG. 5D is a Scanning Electron Microscopy (SEM) image of epinephrine bitartrate (EpiBit) after processing.

DETAILED DESCRIPTION OF THE INVENTION

Figure 1:
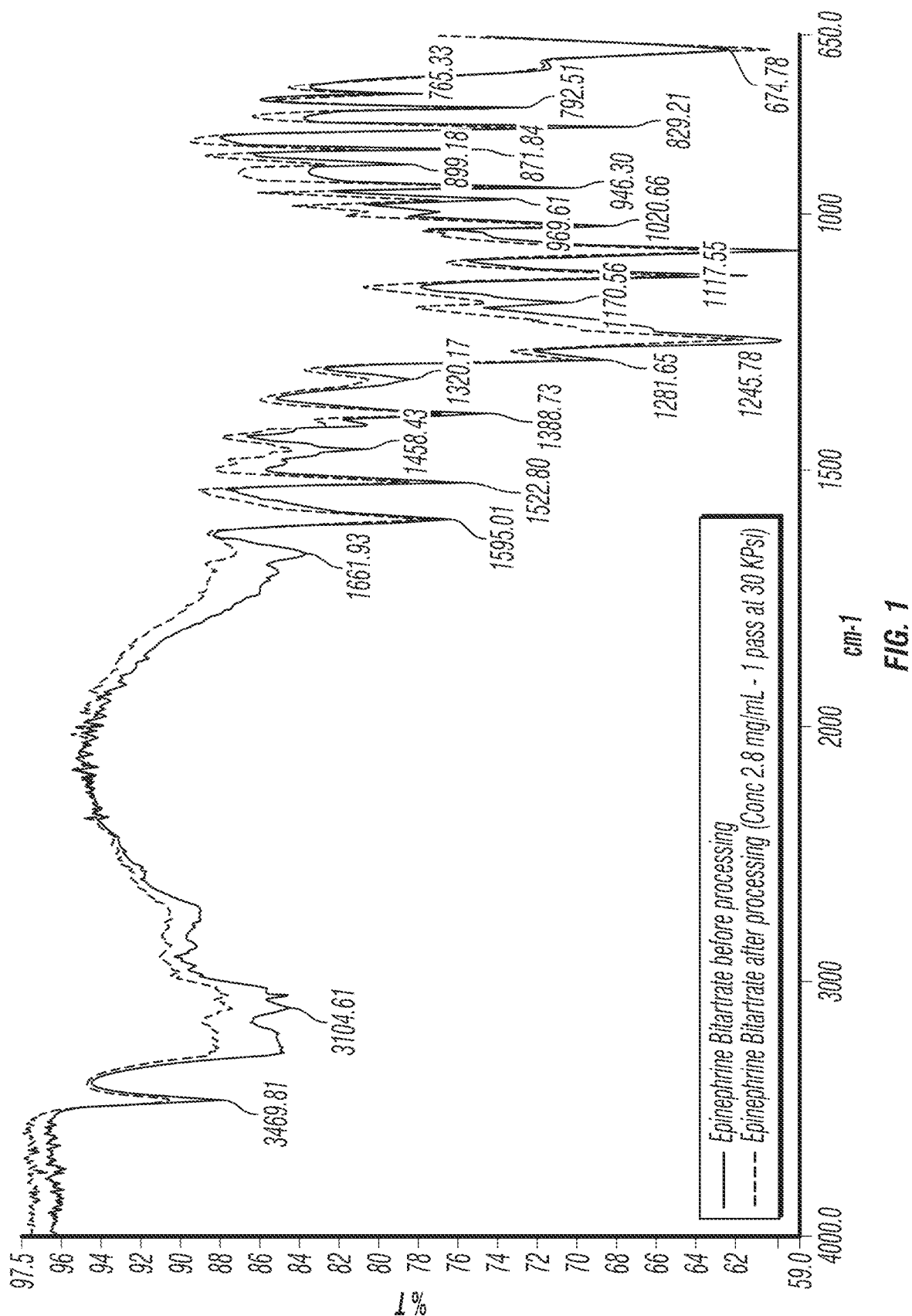
FIG. 1 is an FTIR spectra of epinephrine bitartrate dried particles before and after processing of a 2.8 mg/mL sample processed at 30 KPsi for 1 pass (cycle).

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

Epinephrine (Epi) 0.3 mg IM injection in the thigh is the drug of choice and the only available dosage form for the treatment of anaphylaxis in community sittings. Previously, the instant inventors were able to develop and evaluate rapidly-disintegrating sublingual epinephrine tablets. These studies showed that sublingually administered epinephrine is absorbed and bioequivalent to 0.3 mg IM Injection in a rabbit animal-model.

For the study described herein, it was hypothesized that formulating Epi as nanocrystals (NC) or microcrystals (MC) would significantly enhance its sublingual diffusion. The objectives were to prepare Epi NC or Epi MC and formulate them into rapidly-disintegrating sublingual tablets (ODT) to be tested for their in vitro diffusion, ex vivo diffusion, and in vivo absorption using dialysis membranes, excised sublingual porcine mucosal membranes, and validated rabbit's animal model, respectively.

Epi NC or Epi MC were prepared by top-bottom technique using LV-1 Microfluidizer as described in a previously-filed patent application; U.S. Provisional Patent Application Ser. No. 61/660,273, filed on Jun. 15, 2012. ODTs were manufactured by direct compression using our previously developed and published formulation. The in vitro and ex vivo diffusion of 10, 20, and 40 mg Epi ODT, and 10, 20 mg Epi MC ODT (n=4) were evaluated using static vertical Franz cells. Epi 10 mg solution was used as a control. Mean±SD $JAUC_{0-90}$ of diffused Epi, Jmax, and Epi influx (J) from 40 mg Epi ODT and 20 mg Epi MC ODT were not significantly different from each other both in vitro and ex vivo (p>0.05).

The in vivo absorption of 40 mg Epi ODT and 20 mg Epi MC ODT (n=5) were evaluated in a validated rabbits animal-model. Epi 0.3 mg IM injection in the thigh was used as a positive control and placebo ODT was used as a negative control. The mean±SD $AUC_{0-60}$ and Cmax from 20 mg Epi MC ODT and 40 mg Epi ODT did not differ significantly (p>0.05) from Epi 0.3 mg IM. However, the mean±SD $AUC_{0-60}$ and Cmax of exogenous epinephrine administered through either the sublingual or intramuscular routes differed significantly (p<0.05) from placebo sublingual tablets, endogenous epinephrine.

These micro-sized Epi ODT improved Epi diffusion by two folds and have the potential to reduce the bioequivalent dose of sublingually administered Epi by 50%. These micro-sized Epi ODT have the potential for the first-aid treatment of anaphylaxis in community settings are suitable for phase I studies in humans.

For the emergency treatment of anaphylaxis, prompt intramuscular injection of epinephrine (Epi) in the thigh muscle is the drug of choice[1-4]. Epi auto-injectors such as EpiPen®, EpiPen Jr® (Mylan Inc, Basking Ridge, N.J.), Twinject 0.3 Mg®, and Twinject 0.15® (Shionogi Pharma, Inc. Atlanta, Ga.) are commonly prescribed and the only available dosage form for the first-aid emergency treatment of anaphylaxis in a community setting. However, self-injectable epinephrine is underutilized when anaphylaxis occurs due to several drawbacks[5, 6].

The sublingual route is a promising alternative route for Epi administration. Drugs that can be absorbed sublingually bypass potential metabolic conversion in the gastrointestinal tract and hepatic first-pass metabolism, and reach the systemic circulation in a pharmacologically active form[7-12]. Epi is extensively metabolized after oral administration by the catechol-O-methyltransferase in the gastrointestinal tract and by monoamine oxidase in the gastrointestinal tract and in the liver[13].

The high vascularity of the sublingual mucosa and the low molecular weight of Epi facilitate its rapid absorption directly into the venous circulation through the sublingual and frenular veins. The described rapidly-disintegrating sublingual 40 mg Epi tablets, which retain sufficient hardness to withstand shipping and handling and disintegrate to release Epi rapidly (≤30 sec)[14-16], have shown to be bioequivalent to the adult dose of Epi IM injection, 0.3 mg, in a validated rabbit model[10, 11]. This high dose was essential to create the required concentration gradient that promotes Epi absorption across the sublingual membrane and results in therapeutic plasma drug concentrations.

One of the most common approaches to enhance the rate of drug dissolution and absorption is to significantly reduce its particles size to the micro- or nano-size range. Drug nanocrystals (NC) or microcrystals (MC) are advantageous due to minimal required excipients and almost 100% of the pure drug is produced during the fabrication process[17]. Also, the collected dried drug NC or MC can be formulated into various dosage forms.

In designing the experiments described herein, it was hypothesized that using reduced particle size of Epi instead of regular raw Epi crystals will significantly increase Epi dissolution rate and absorption. Also, they would reduce the required bioequivalent dose to Epi 0.3 mg IM injections.

In the study described herein, the in vitro and ex vivo diffusion of epinephrine bitartrate microcrystals (EpiBit MC) against regular epinephrine bitartrate (EpiBit) crystals formulated into our rapidly-disintegrating tablets (ODT) was tested to evaluate the permeability of these micro-sized Epi ODT before performing in vivo studies.

In the in vivo study, the absorption of epinephrine bitartrate microcrystals (EpiBit MC) and regular epinephrine bitartrate (EpiBit) crystals formulated into our rapidly-disintegrating tablets (ODT) was tested against the standard Epi 0.3 mg IM injection in the thigh. The aim was to establish a significantly lower bioequivalent sublingual dose of Epi than the one previously achieved.

These rapidly-disintegrating sublingual epinephrine tablets will have the potential as user-friendly, non-invasive alternative for the first-aid emergency treatment of anaphylaxis in a community setting.

Materials

These materials are useful for the in vitro and ex vivo diffusion studies described below and for the fabrication of epinephrine fine particles and tablets.

(−)-Epinephrine (+) bitartrate was purchased from Sigma-Aldrich (St. Louis, Mo.). Ceolus® PH-301 (microcrystalline cellulose) with a mean particle size of 50 µm was supplied by Asahi Kasei Chemicals Corp (Tokyo, Japan) and low-substituted hydroxypropyl cellulose (LH11) with a mean particle size of 50 µm was supplied by Shin-Etsu Chemical Co (Tokyo, Japan). Magnesium stearate was purchased from Mallinckrodt Baker (Phillipsburg, N.J.). Isopropyl alcohol, 99.5%, was purchased from BDH (VWR, West Chester, Pa.). Spectra/Por® 7 dialysis membranes with 1000 Dalton MWCO were purchased from Spectrum Laboratories, Inc. (Rancho Dominguez, Calif.). Potassium phosphate monobasic was purchased from Sigma-Aldrich (St. Louis, Mo.) and sodium hydroxide was purchased from J. T. Baker (Philipsburg, N.J.).

Fabrication and Characterization of Epinephrine Fine Particles Using High Shear Fluid Processor (Microfluidizer)-Homogenization Method Epinephrine bitartrate fine particles were fabricated, developed, and characterized as described in the previously-filed related application; U.S. Provisional Patent Application Ser. No. 61/660,273, filed on Jun. 15, 2012.

Preparation of Epinephrine Bitartrate Nanocrystals

The EpiBit NC (or EpiBit MC) was prepared by a top-bottom technique using LV-1 High Sheer Fluid Processor "Microfluidizer" (Microfluidics, Newton, Mass.) equipped with G10Z reaction chamber. Briefly, epinephrine bitartrate (2.8 mg/mL), (with and without the use of any excipients), was suspended in 6 mL isopropyl alcohol, sonicated for 30 seconds and injected into the system. The suspension was processed at 30,000 Psi for one cycle. The microfluidizer-receiving coil was immersed in ice to reduce the heat produced during the process. The nanosuspension was centrifuged using Avanti J-25 centrifuge (Beckman Coulter, Inc, Miami, Fla.) at 15,000 rpm and 15° C. for 30 minutes. The upper clear solvent was removed by aspiration and the remaining particles were dried by vacuum concentrator at room temperature.

Characteristics of the Epinephrine Bitartrate Nanocrystals
Particle Size and Zeta Potential Measurement The average particles size (by volume) of EpiBit before processing was measured using laser diffraction technique using Mastersizer (Malvern Instruments Inc, Westborough, Mass.). D (0.1), D (0.5) or median, D (0.9), and D (4, 3) or mean volume are shown in Table 1. Mean±SD particles size distribution (by volume) of EpiBit crystals before processing was 131.8±10.5 µm (n=6). The 10$^{th}$ percentile (Dv0.1), median (Dv0.5), and 90$^{th}$ percentile (Dv0.9) were 39.8±3.0 µm, 113.6±9.1 µm, and 254.8±20.1 µm, respectively.

TABLE 1

Particles Size Distribution (by Volume) of EpiBit Before Processing Before Fabrication (µm)

| Sample # | D (4, 3) | D (0.1) | D (0.5) | D (0.9) |
|---|---|---|---|---|
| 1 | 147.1 | 44.4 | 128.0 | 282 |
| 2 | 129.5 | 40.27 | 111.4 | 249.6 |
| 3 | 121.6 | 37.4 | 105.2 | 234.7 |
| 4 | 136.0 | 41.0 | 117.5 | 262 |
| 5 | 137.2 | 40.25 | 116.1 | 269.6 |
| 6 | 119.2 | 35.7 | 103.3 | 230.7 |

TABLE 1-continued

Particles Size Distribution (by Volume) of EpiBit Before Processing Before Fabrication (µm)

| Sample # | D (4, 3) | D (0.1) | D (0.5) | D (0.9) |
|---|---|---|---|---|
| Mean | 131.8 | 39.8 | 113.6 | 254.8 |
| Standard Deviation | 10.5 | 3.0 | 9.1 | 20.1 |

The Z-average particles size (by intensity) and the average zeta potential of EpiBit after processing were measured using light scattering technique using Zetasizer ZS90 (Malvern Instruments Inc, Westborough, Mass.). Z-average with polydispersity index (Pdi) and zeta potential are shown in Table 2.

Mean (±SD) particles size distribution by intensity and by volume, Pdi, and zeta potential (n=3) of EpiBit crystals after processing using the microfluidizer for one cycle at 30,000 Psi were 2.4±0.4 2.5±0.4 0.185±0.019, and −4.5±1.4 mV, respectively.

The processing of EpiBit results in fine particles with a mean particle size at the low end of the micro-size range but approaching the nano-size range. The particles of this size range were used for diffusion studies and in vivo animal studies.

TABLE 2

Particles Size Distribution (by intensity) and zeta potential of EpiBit After Processing After Fabrication

| Sample # | Z-average (d · nm) | Pdi | Z-potential (mV) |
|---|---|---|---|
| 1 | 2649 | 0.187 | −6.0 |
| 2 | 1958 | 0.165 | −3.4 |
| 3 | 2615 | 0.202 | −4.0 |
| Mean | 2407.3 | 0.185 | −4.5 |
| Standard Deviation | 389.5 | 0.019 | 1.4 |

Fourier Transformation InfraRed (FT-IR)

The processed EpiBit were tested for stability and removal of isopropyl alcohol using FT-IR spectrometer, spectrum 100 (PerkinElmer, Waltham, Mass.) scanned from 4000-650 cm$^{-1}$. The FT-IR spectrum of EpiBit before and after processing is shown in FIG. 1. There was no evidence of EpiBit degradation after processing as the spectra before and after processing were similar.

Figure 2:
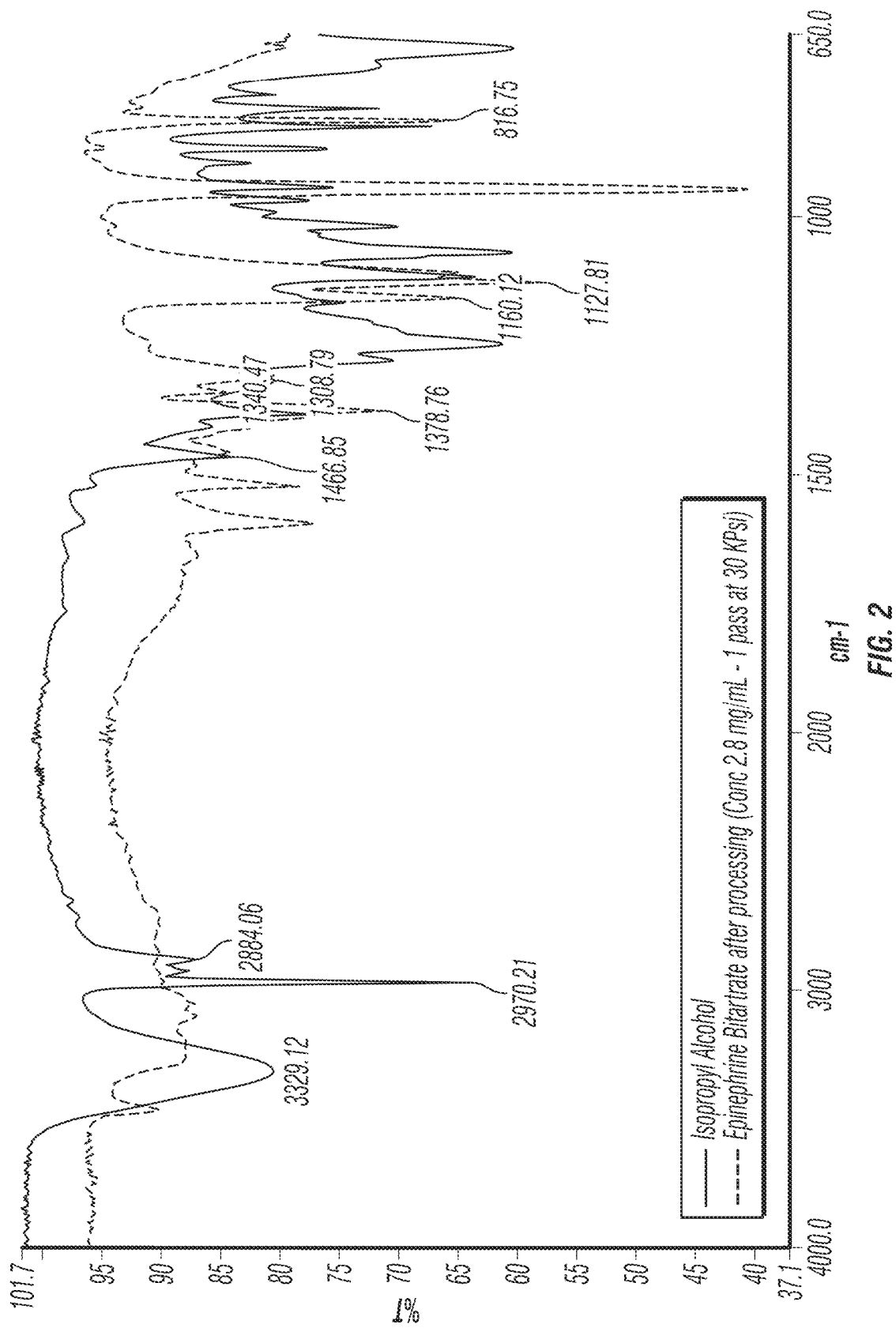
FIG. 2 is an FTIR spectra of epinephrine bitartrate dried particles after processing of a 2.8 mg/mL sample processed at 30 KPsi for 1 pass (cycle) and isopropyl alcohol.

The FT-IR spectrum of isopropyl alcohol and EpiBit after processing is shown in FIG. 2. The isopropyl alcohol peaks are missing, which indicates successful removal of the isopropyl alcohol. Thus, there was no evidence of isopropyl alcohol remaining in the EpiBit particles after drying as shown in the spectrum of processed EpiBit.

Differential Scanning Calorimetry (DSC)

Figure 3:
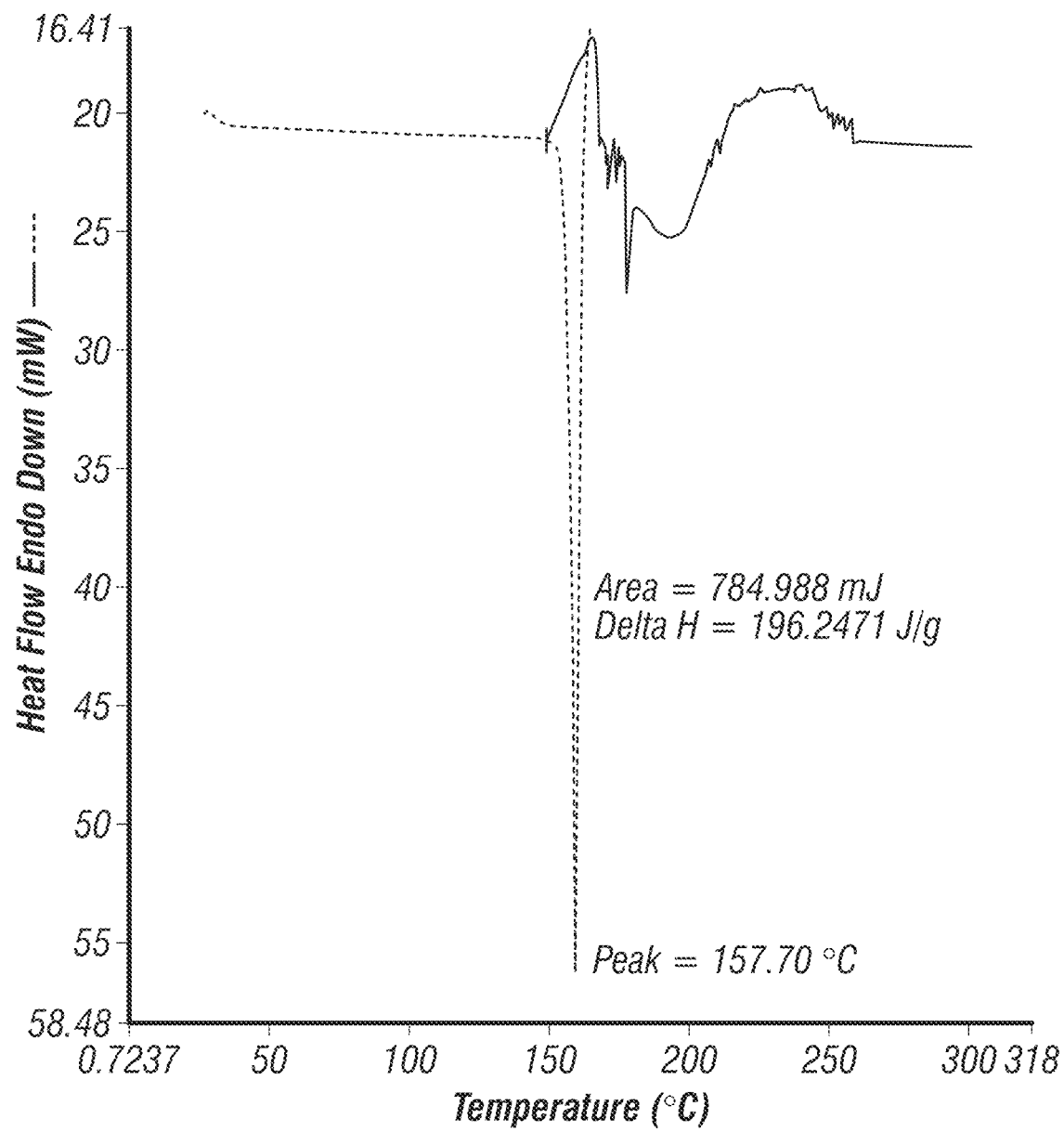
FIG. 3 is a Differential Scanning calorimetry (DSC) spectrum of epinephrine bitartrate (EpiBit) before processing.
Figure 4:
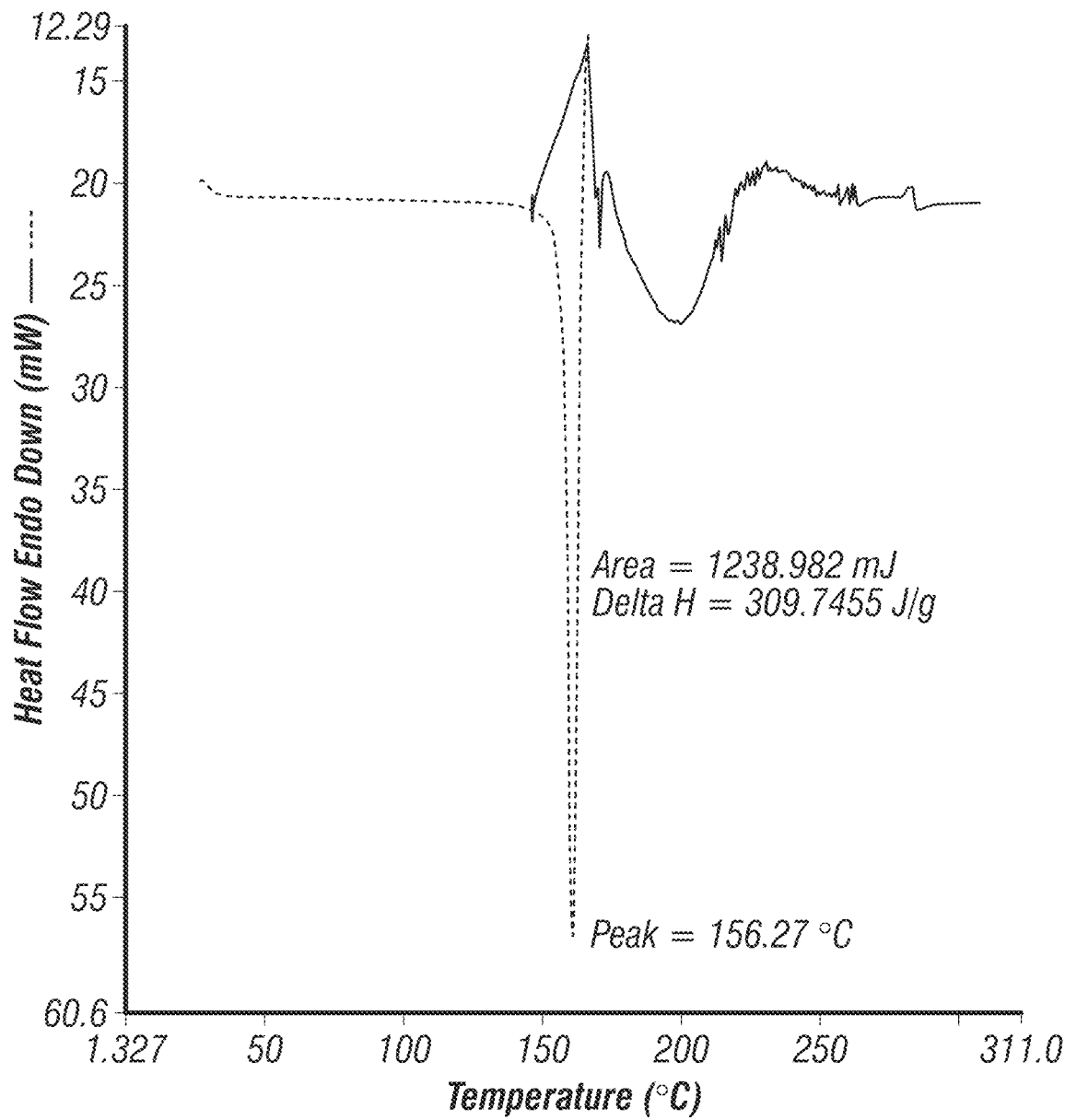
FIG. 4 is a Differential Scanning calorimetry (DSC) spectrum of epinephrine bitartrate (EpiBit) after processing.
Figure 5A:
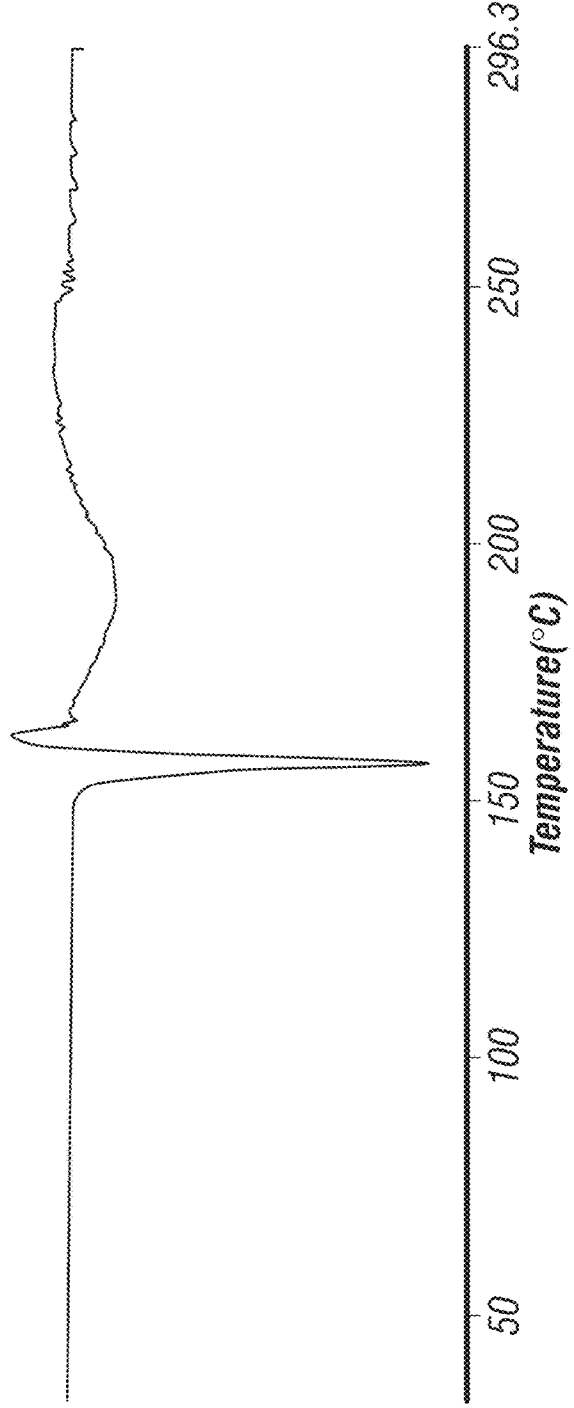
FIGS. 5A-D.
Figure 5B:
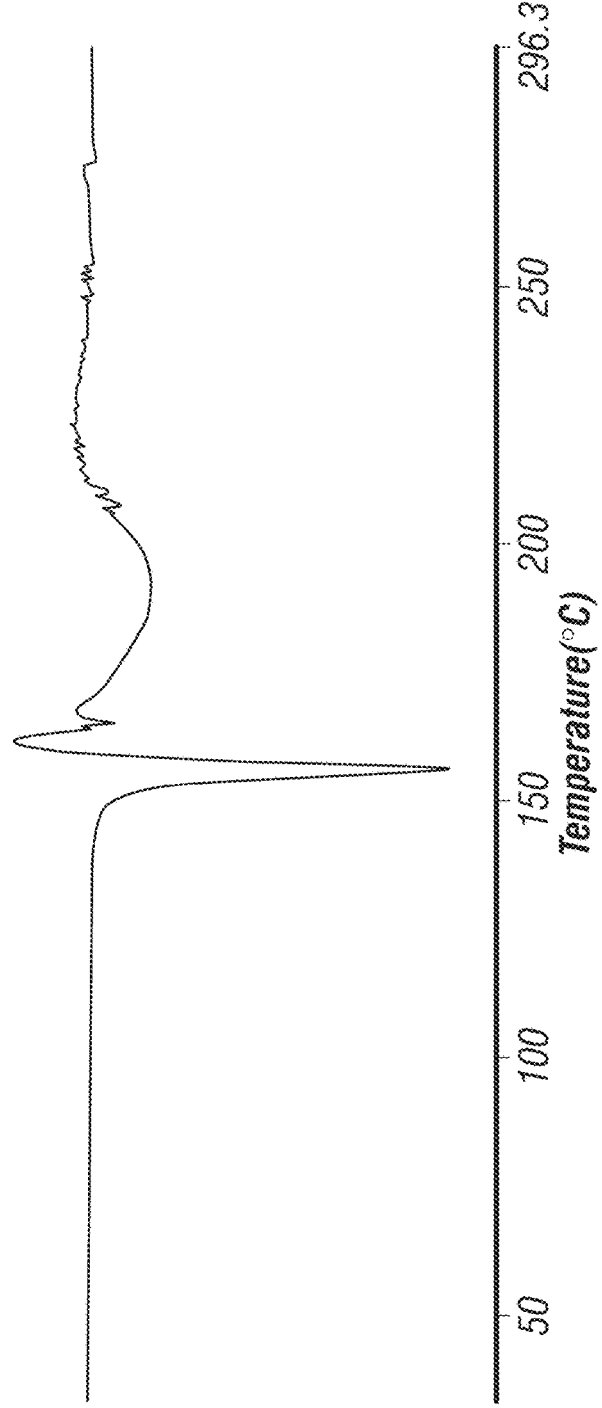

Also, the processed EpiBit were tested for purity, stability, and crystallinity changes using Differential Scanning calorimetry (DSC) 4000 (PerkinElmer, Waltham, Mass.) that was calibrated using an indium standard and heated from 30 to 300° C. at rate of 10° C./min and with a nitrogen purge of 20 mL/min. The DSC spectra of EpiBit before and after processing are shown in FIGS. 3 and 4, respectively. There was no evidence of EpiBit degradation or crystallinity change after processing. FIG. 5A shows another view of a DSC spectrum of EpiBit before processing and FIG. 5B shows another view of a DSC spectrum after processing. These spectra (FIGS. 5A and 5B) are similar before and after processing.

Scanning Electron Microscopy (SEM)

Figure 5C:
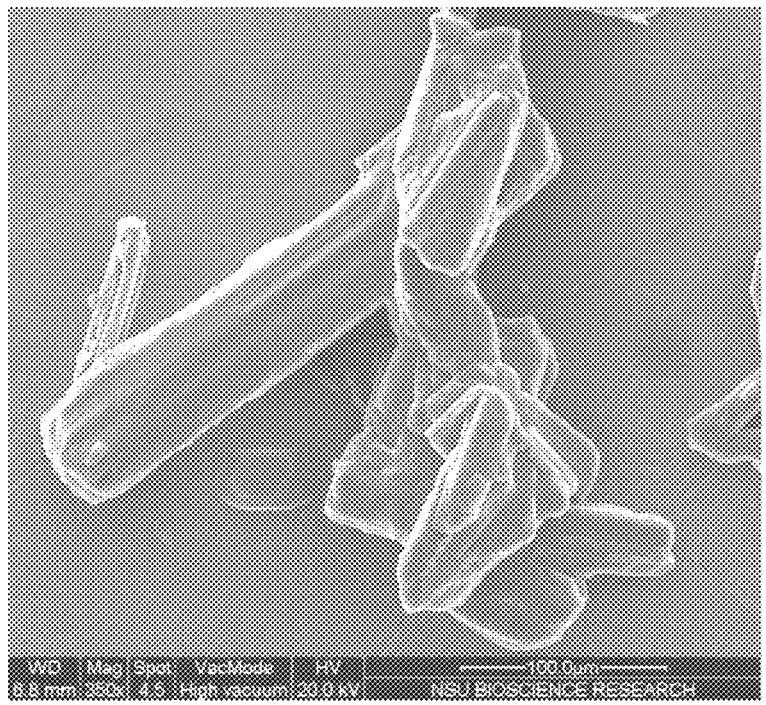
Figure 5D:
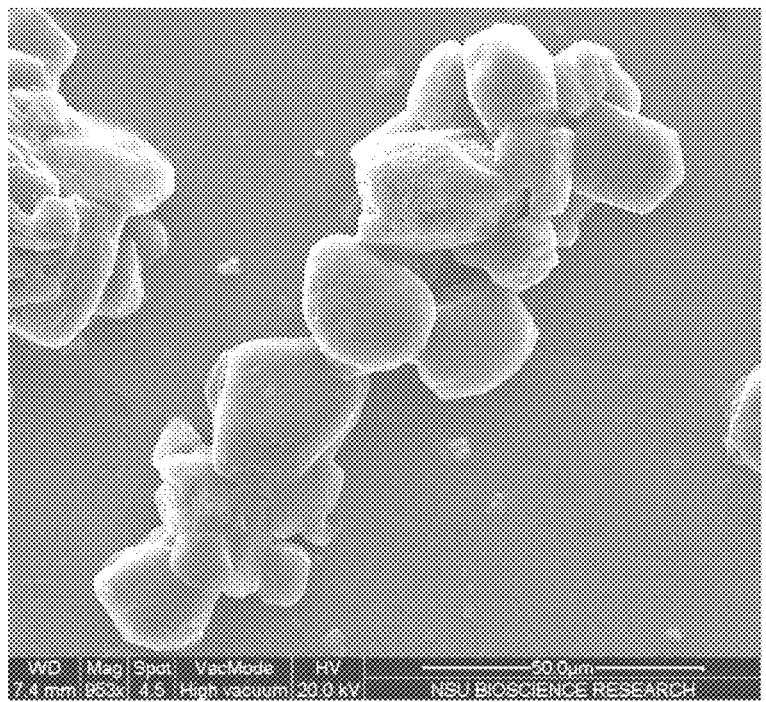

The morphologies of EpiBit before and after processing were examined using Quanta 200 Environmental Scanning Electron Microscope (FEI, Hillsboro, Oreg.) operated at an accelerating voltage of 20 kV. Fresh suspension of processed EpiBit and a fresh dispersion of unprocessed EpiBit were deposited on an aluminum stub following the evaporation of isopropyl alcohol and sputter coated with gold using Cressington 108 sputter coater (Cressington Scientific Instruments Ltd, Watford, England). The Scanning Electron Microscopy (SEM) images of EpiBit before and after processing are shown in FIGS. 5C and 5D, respectively. There was a morphological change in the EpiBit crystals from a rectangular shape before processing to a smaller, spherical shape after processing.

Rapidly-Disintegrating Epinephrine Sublingual Tablet Formulation

Rapidly-disintegrating tablets for sublingual administration were developed and evaluated as described in the previously-filed related applications; U.S. Utility patent application Ser. No. 11/672,503, filed on Feb. 7, 2007 and U.S. Utility patent application Ser. No. 11/530,360, filed on Sep. 8, 2006. A range of epinephrine (Epi) doses were formulated as rapidly-disintegrating tablets using equivalent amounts of regular L-epinephrine bitartrate (EpiBit) obtained from Sigma-Aldrich or nanocrystals (NC) or microcrystals (MC) of EpiBit fabricated as previously described. Tablets containing 10, 20, and 40 mg Epi and 10 and 20 mg Epi MC were manufactured using equivalent amounts of EpiBit.

Manufacturing and Quality Control of Tablets for In Vitro and Ex Vivo Diffusion Studies Five ODT formulations containing EpiBit equivalent to 10 mg, 20 mg, and 40 mg, epinephrine and EpiBit MC equivalent to 10 mg and 20 mg epinephrine were manufactured by direct compression. These tablets were formulated using microcrystalline cellulose, low-substituted hydroxylpropyl cellulose, and magnesium stearate as described in our previous studies[15, 16]. The tablet weight was 150 mg. All excipients were used as supplied and kept under low humidity condition before mixing. The mixing process was performed in a nitrogen-preflushed opaque glass container using three-dimensional manual mixer (Inversina, Bioengineering AG, Wald, Switzerland). The powder mixture of the five tablet formulations was compressed right after mixing using 4-stations Colton rotary press (Key Industries, Englishtown, N.J.) at a pre-selected compression force for each tablet formulation, based on our previous results' to ensure sufficient hardness to withstand shipping and handling while maintaining rapid tablet disintegration.

All tablet formulations were tested for quality control as follows:

Dimensions:

Six tablets were randomly selected from each formulation. The diameter and the thickness of rapidly-disintegrating Epi tablets were measured using digital caliper with a range of 0-100 mm and accuracy of 0.02 (Harbor Freight Tools, Camarillo, Calif.). The mean±SD (mm) and RSD % of tablets' diameters and thicknesses are shown in Table 3.

Hardness:

Six tablets were randomly selected from each formulation. The hardness or the breaking force of rapidly-disintegrating Epi tablets was measured using Hardness Tester LIH-3 (Vanguard, Spring, Tex.). The mean±SD (Kgf) and RSD % of hardness for various tablet formulations are shown in Table 3.

Disintegration Time:

Six tablets were randomly selected from each formulation. The disintegration time of rapidly-disintegrating Epi tablets was measured using a previously developed and published method to discriminate between the disintegration times of rapidly-disintegrating tablets or orally disintegrating tablets[15, 16]. The mean±SD (Sec) and RSD % of disintegration time for various tablet formulations are shown in Table 3.

USP Weight Variation Test:

Tablet weight variation was measured using the USP methods and criteria[18]. The mean±SD (%) and RSD % of weight variation for various tablet formulations are shown in Table 3.

USP Content Uniformity Test:

Tablet drug content uniformity was measured using the USP methods and criteria[18]. Drug content was analyzed using a High Performance Liquid Chromatography (HPLC) system with ultraviolet detection (UV) (PerkinElmer, Waltham, Mass.) according to USP[19]. The mean±SD (%) and RSD % of content uniformity for various tablet formulations are shown in Table 3.

USP Friability Test:

The friability of rapidly-disintegrating Epi tablets was measured using USP Friability Tester LIC-1 (Vanguard, Spring, Tex.) according to USP methods and criteria[18]. The mean tablets weight loss (%) for various tablet formulations are shown in Table 3.

Mean±SD hardness, disintegration time, weight variation, content uniformity, and friability for 10 mg, 20 mg, and 40 mg Epi, and 10 mg and 20 mg Epi MC tablets are shown in Table 3. All tablet formulations were within UDP criteria for weight variation, drug content uniformity, and friability[18, 20].

TABLE 3

The mean ± SD hardness (n = 6), disintegration time, weight variation, content uniformity, tablet diameter, tablet thickness, and friability for 10 mg, 20 mg, and 40 mg tablet formulations*

| Formulations | Tablets Characteristics* | | | | | | |
|---|---|---|---|---|---|---|---|
| | H | DT | WV (RSD %) | CU (RSD %) | D | T | F |
| 10 mg Epi Tablets | 1.7 ± 0.3 | 16.3 ± 0.3 | 100.0 ± 0.0 (0.0) | 100.6 ± 4.0 (4.0) | 7.9 ± 0.0 | 3.5 ± 0.0 | 0.4 |
| 20 mg Epi Tablets | 1.6 ± 0.1 | 15.8 ± 0.4 | 99.9 ± 0.7 (0.7) | 97.7 ± 2.7 (2.7) | 7.9 ± 0.0 | 3.9 ± 0.0 | 0.5 |
| 40 mg Epi Tablets | 1.7 ± 0.2 | 31.3 ± 0.4 | 100.0 ± 0.6 (0.6) | 95.6 ± 2.4 (2.5) | 7.9 ± 0.0 | 3.4 ± 0.0 | 0.6 |
| 10 mg Epi MC Tablets | 2.5 ± 0.0 | 5.5 ± 0.7 | 99.7 ± 1.2 (1.2) | 92.9 ± 0.3 (0.3) | 8.0 ± 0.1 | 3.7 ± 0.0 | NA |
| 20 mg Epi MC Tablets | 2.5 ± 0.1 | 8.7 ± 0.3 | 98.3 ± 1.7 (1.7) | 92.2 ± 4.2 (4.5) | 8.0 ± 0.1 | NA | NA |

*H indicates tablet hardness (kgf); DT, disintegration time (sec); WV, weight variation (%); CU, content uniformity (%); RSD, relative standard deviation (%); D, tablet diameter (mm); T, tablet thickness (mm); F, Friability (%).

Manufacturing and Quality Control of Tablets for In Vivo Absorption Studies

Additionally, five ODT formulations containing EpiBit equivalent to 0 mg and 40 mg Epi and EpiBit MC equivalent to 20 mg Epi were manufactured by direct compression. These tablets were formulated and manufactured using the same excipients and method in our previous studies[15, 16]. All tablet formulations were tested for tablet weight variation, drug content uniformity, and friability using the harmonized USP methods and criteria[18, 20]. Also, they were tested for disintegration time using a novel in vitro disintegration test developed to simulate the sublingual environment[15, 16] Drug content was analyzed using a high performance liquid chromatography (HPLC) system with ultra violet (UV) detection (PerkinElmer, Waltham, Mass.) according to USP method for Epi injections[19].

These tablets did not contain lactose or bisulfite and met USP standards for tablet weight variation, content uniformity, and friability[18, 20.] They also disintegrated in less than 30 seconds.

Methods for In Vitro and Ex Vivo Diffusion Studies

The in vitro and ex vivo diffusion of EpiBit MC and EpiBit formulated into ODT were evaluated using static vertical jacketed Franz Cells with OD of 20 mm and reservoir volume of 20±1 mL (PermeGear Inc., Hellertown, Pa.). For in vitro diffusion studies, 7 Spectra/Por® dialysis membranes with 1000 Dalton MWCO (Spectrum Laboratories, Inc., Rancho Dominguez, Calif.) were used as the diffusion membranes. For ex vivo diffusion studies, sublingual mucosa (floor of the mouth) were excised from pigs and used as the diffusion membranes. Frozen pig's heads were obtained from a local abattoir and defrosted at room temperature. The porcine mucosa were excised by dissecting the sublingual mucosa and removing the underlying connective tissue using a scalpel and fine tweezers using established surgical technique. The excised mucosa were inspected for integrity and then frozen on aluminum foil at −20° C. until used (<4 weeks). The mucosal membranes were defrosted at room temperature before each experiment.

Four ODT containing EpiBit equivalent to 10, 20, and 40 mg Epi or EpiBit MC equivalent to 10, and 20 mg Epi were tested in vitro and ex vivo. EpiBit equivalent to 10 mg Epi was dissolved in 1 mL of the diffusion medium and used as a control (n=4).

The receptor chamber that has a magnetic stirrer was filled with phosphate buffer, pH 5.8 (saliva average pH), as the diffusion medium. Air bubbles were removed after mounting the membrane between the donor and receptor chambers and before the beginning of the experiment. The water bath was set at 37° C. and water was circulated in the jacketed Franz Cells. The mounted membranes were equilibrated with the diffusion medium for 30 minutes from both sides before the experiment and were checked for any leaks.

The tested tablet was placed at the center of the donor chamber on the membrane at $T_0$ and 2 mL of the diffusion medium was added to facilitate tablet disintegration and dissolution. Aliquots, 200 μL, were withdrawn from the receptor chamber using 6 inch-long needles (Popper &Sons, Inc, New Hyde Park, N.Y.) and 1 mL syringes at 5, 10, 15, 20, 30, 45, 60, 75, and 90 min. The withdrawn volumes were replaced with fresh medium. Samples were transferred to HPLC vials for HPLC analysis using UV detector as described below.

Epinephrine HPLC Analysis

Samples from tablets for content uniformity test and from diffusion studies were analyzed for Epi content according to USP method for Epi injection analysis[19] using HPLC system with UV detection (PerkinElmer, Waltham, Mass.). The calibration curve was linear over the range of 6.25 to 200.0 m/mL with correlation of coefficients ($R^2$) of >0.99 (n=5). The coefficient of variation (RSD %) of the system reproducibility at concentrations of 6.25 and 200 m/mL (n=5 each) were 1.07% and 0.40%, respectively. The intra- and inter-assay RSD % were 0.40% and 0.70% (n=2) and 2.8% and 1.5% (n=3), respectively.

Data Analysis

The mean±SD cumulative diffused Epi per area (μg/cm$^2$) and percentage of diffused Epi for each ODT formulation were calculated. The mean±SD Epi influx, J (μg/cm$^2$/min), and lag time, tL (min), were calculated from the slope and the intercept with the x-axis of each graph (n=4). Also, Epi permeability, P (cm/min), was calculated by dividing J by Epi concentration in the donor chamber at $T_0$. The area under the curve of diffused Epi per area, $JAUC_{0-90}$ (μg/cm$^2$/min); the maximum Epi diffused, Jmax (μg/cm$^2$); and the time to reach Jmax, Tmax (min) were calculated using WinNonlin software (Pharsight, Mountain View, Calif.). Data were statistically compared by one-way ANOVA and Tukey-Kramer tests using NCSS statistical software (NCSS, Kaysville, Utah). Differences were considered to be statistically significant at $p<0.05$.

Results

1) The In Vitro Diffusion of Epinephrine Microcrystals Sublingual Tablets

Figure 6:
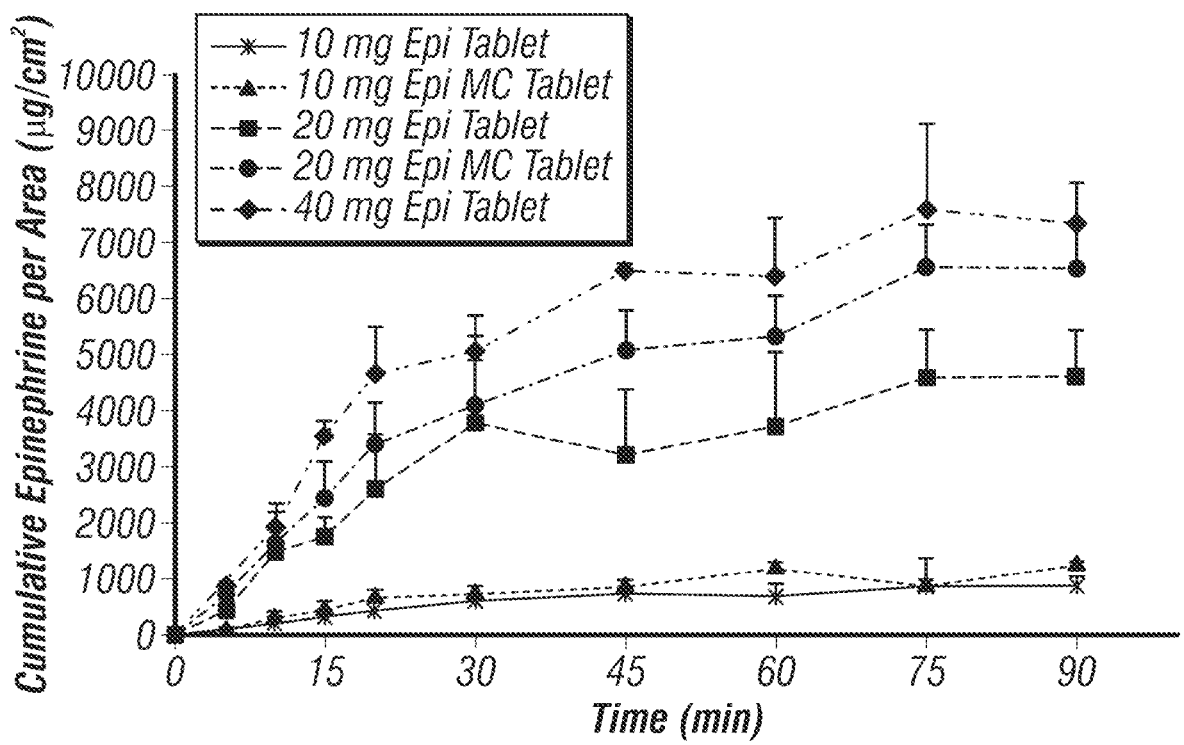
FIG. 6 shows the mean±SD (n=4) cumulative diffused epinephrine per dialysis membrane area versus time.
Figure 7:
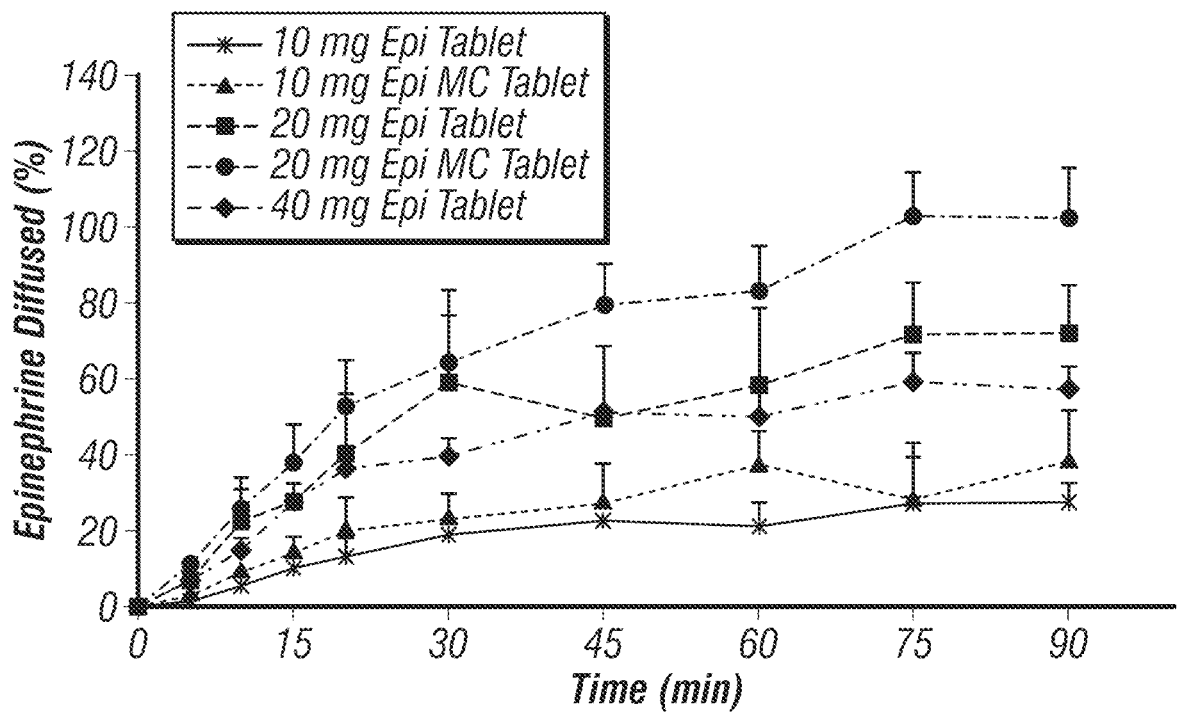
FIG. 7 shows the mean±SD (n=4) percentage of diffused epinephrine through dialysis membrane versus time.

The mean±SD (n=4) cumulative diffused Epi per area and percentage of diffused Epi for each formulation through dialysis membrane are shown in Tables 4 and 5, and illustrated in FIGS. 6 and 7, respectively.

TABLE 4

Mean ± SD (n = 4) cumulative diffused epinephrine per area (μg/cm$^2$) for each formulation through dialysis membrane.

| Time (min) | 10 mg Epi Tablet | 10 mg Epi MC Tablet | 20 mg Epi Tablet | 20 mg Epi MC Tablet | 40 mg Epi Tablet |
| --- | --- | --- | --- | --- | --- |
| 5 | 62.1 ± 9.3 | 99.2 ± 30.9 | 456.1 ± 130.5 | 735.8 ± 101.0 | 835.2 ± 107.8 |
| 10 | 183.9 ± 25.0 | 321.8 ± 153.9 | 1499.6 ± 694.8 | 1642.4 ± 370.1 | 1934.6 ± 391.7 |
| 15 | 329.5 ± 7.6 | 466.7 ± 123.4 | 1764.3 ± 337.7 | 2431.0 ± 659.0 | 3573.7 ± 240.0 |
| 20 | 436.2 ± 142.4 | 668.4 ± 262.0 | 2600.7 ± 996.2 | 3386.2 ± 770.8 | 4673.6 ± 833.3 |
| 30 | 606.3 ± 91.4 | 744.5 ± 223.4 | 3781.5 ± 1127.9 | 4112.5 ± 1235.6 | 5075.7 ± 625.2 |
| 45 | 731.9 ± 90.3 | 873.4 ± 339.0 | 3207.6 ± 1180.6 | 5085.0 ± 698.4 | 6504.1 ± 105.3 |
| 60 | 683.2 ± 201.9 | 1198.9 ± 288.5 | 3739.7 ± 1315.3 | 5325.4 ± 745.5 | 6421.7 ± 1041.7 |
| 75 | 876.3 ± 497.1 | 906.7 ± 364.6 | 4602.4 ± 857.2 | 6568.8 ± 755.3 | 7585.8 ± 1554.4 |
| 90 | 888.1 ± 149.7 | 1235.3 ± 419.9 | 4614.7 ± 824.0 | 6554.1 ± 804.0 | 7337.4 ± 725.6 |

TABLE 5

Mean ± SD (n = 4) percentage of diffused epinephrine (%) for each formulation through dialysis membrane.

| Time (min) | 10 mg Epi Tablet | 10 mg Epi MC Tablet | 20 mg Epi Tablet | 20 mg Epi MC Tablet | 40 mg Epi Tablet |
|---|---|---|---|---|---|
| 5  | 2.0 ± 0.3  | 3.1 ± 1.0   | 7.2 ± 2     | 11.6 ± 1.6  | 6.6 ± 0.8  |
| 10 | 5.8 ± 0.8  | 10.1 ± 4.8  | 23.5 ± 10.9 | 25.8 ± 5.8  | 15.2 ± 3.1 |
| 15 | 10.4 ± 2.5 | 14.7 ± 3.9  | 27.7 ± 5.3  | 38.2 ± 10.3 | 28.1 ± 1.9 |
| 20 | 13.8 ± 4.6 | 21.0 ± 8.2  | 40.8 ± 15.6 | 53.2 ± 12.1 | 36.7 ± 6.5 |
| 30 | 19.1 ± 2.9 | 23.4 ± 7.0  | 59.4 ± 17.7 | 64.6 ± 19.4 | 39.8 ± 4.9 |
| 45 | 23.1 ± 2.8 | 27.4 ± 10.6 | 50.4 ± 18.5 | 79.8 ± 11.0 | 51.1 ± 0.8 |
| 60 | 21.6 ± 6.4 | 37.6 ± 9.1  | 58.7 ± 20.7 | 83.6 ± 11.7 | 50.4 ± 8.2 |
| 75 | 27.7 ± 15.8| 28.5 ± 11.4 | 72.3 ± 13.5 | 103.1 ± 11.9| 59.5 ± 12.2|
| 90 | 28.0 ± 4.7 | 38.8 ± 13.2 | 72.5 ± 12.9 | 102.9 ± 12.6| 57.6 ± 5.7 |

The mean (±SD) Epi $JAUC_{0-90}$, Jmax, Tmax, J, P, and $t_1$ are shown in Table 6. Also, Epi J and P for each formulation are illustrated in FIGS. 8 and 9, respectively.

The mean (±SD) Epi $JAUC_{0-90}$ and Jmax of 40 mg Epi tablets (484184.9±29655.9 µg/cm$^2$/min and 7508.3±568.7 µg/cm$^2$, respectively) and 20 mg Epi MC tablets (402852.2±55299 µg/cm$^2$/min and 6727.2±736.3 µg/cm$^2$, respectively) were not significantly different (p>0.05) from each other and were significantly higher (p<0.05) than the rest of the formulations (FIG. 6 and Table 6). The Epi Tmax was not significantly different (p>0.05) between all formulations (Table 6).

Figure 8:
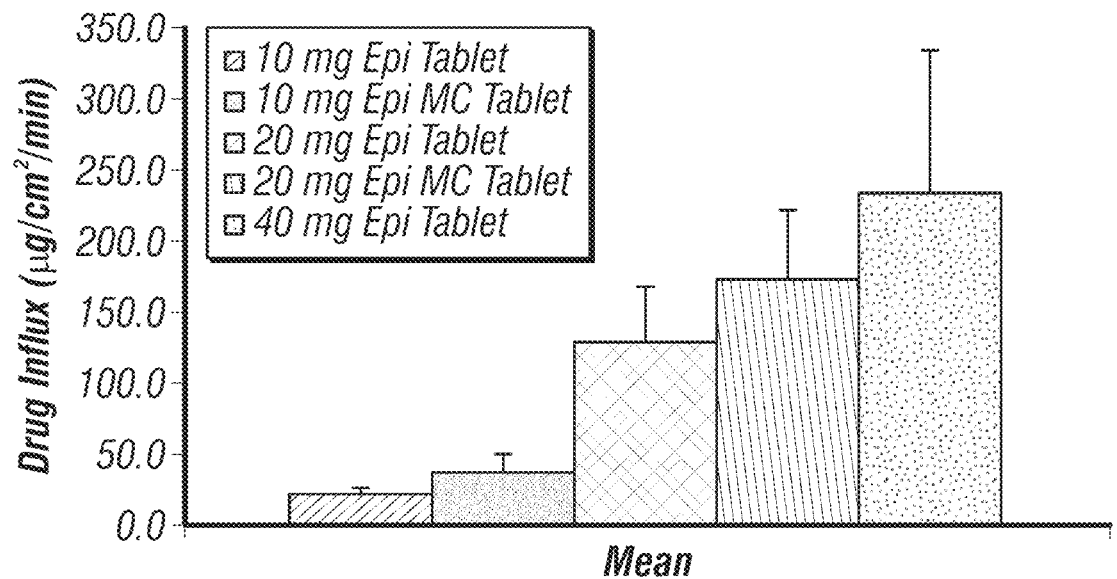
FIG. 8 shows the mean±SD (n=4) of epinephrine influx (J) through dialysis membrane.

The mean (±SD) Epi J of 40 mg Epi tablets (234.2±99.6 µg/cm$^2$/min) and 20 mg Epi MC tablets (172.2±49.8 µg/cm$^2$/min) were not significantly different (p>0.05) from each other and were significantly higher (p<0.05) than the 10 mg Epi tablets and 10 mg Epi MC tablets (FIG. 8 and Table 6). The Epi $t_L$ was not significantly different (p>0.05) between all formulations (Table 6).

Figure 9:
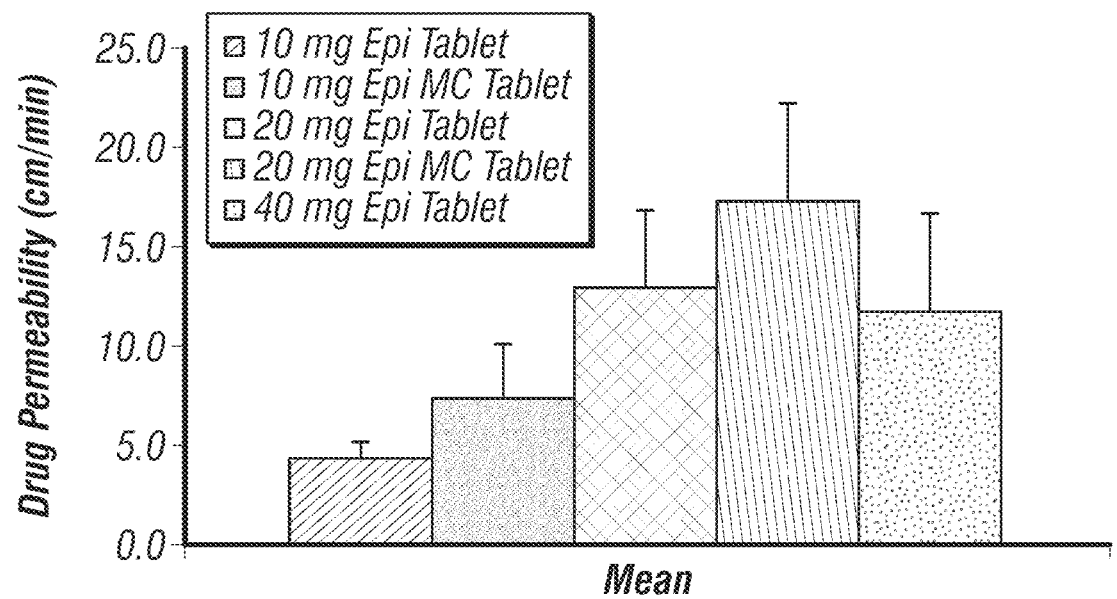
FIG. 9 shows the mean±SD (n=4) of epinephrine permeability (P) through dialysis membrane.

The mean (±SD) Epi P of 20 mg Epi MC tablets (17.2±5.0 cm/min) was significantly higher (p<0.05) than the rest of the formulations (FIGS. 7 and 9, and Table 6).

TABLE 6

Mean ± SD (n = 4) of epinephrine $JAUC_{0-90}$, Jmax, Tmax, J, P, and $t_L$ for each formulation through dialysis membrane.

| | 10 mg Epi Tablet | 10 mg Epi MC Tablet | 20 mg Epi Tablet | 20 mg Epi MC Tablet | 40 mg Epi Tablet |
|---|---|---|---|---|---|
| $JAUC_{0-90}$ (µg/cm$^2$/min) | 54604.1 ± 11332.5 | 72461 ± 21229.2 | 292089 ± 58875.7 | 402852.2 ± 55299 | 484184.9 ± 29655.9 |
| Jmax (µg/cm$^2$) | 1070.8 ± 384.2 | 1297.8 ± 305.3 | 5093.8 ± 249.5 | 6727.2 ± 736.3 | 7508.3 ± 568.7 |
| Tmax (min) | 78.8 ± 14.4 | 82.5 ± 15.0 | 71.3 ± 28.4 | 86.3 ± 7.5 | 82.5 ± 8.7 |
| J (µg/cm$^2$/min) | 22.1 ± 4.1 | 37.0 ± 13.6 | 128.6 ± 39.2 | 172.2 ± 49.8 | 234.2 ± 99.6 |
| P (cm/min) | 4.4 ± 0.8 | 7.4 ± 2.7 | 12.9 ± 3.9 | 17.2 ± 5.0 | 11.7 ± 5.0 |
| $t_L$ (min) | 1.4 ± 0.9 | 2.0 ± 0.8 | 0.5 ± 1.0 | 0.0 ± 0.0 | 1.6 ± 1.4 |

$JAUC_{0-90}$, area under the curve of diffused Epi per area versus time;

Jmax, the maximum Epi diffused;

Tmax, the time to reach Jmax;

J, Epi influx;

P, Epi permeability;

$t_L$, lag time.

The JAUC, Jmax, J, P for 20 mg Epi MC tablets was not significantly different (p>0.05) from 40 mg Epi tablets in vitro. The reduction of EpiBit particles size close to the nano-size range increased EpiBit influx two folds, which presents a great potential for these reduced-sized Epi ODT to reduce the required Epi sublingual dose by half.

2) The Ex Vivo Diffusion of Epinephrine Microcrystals Sublingual Tablets

Figure 10:
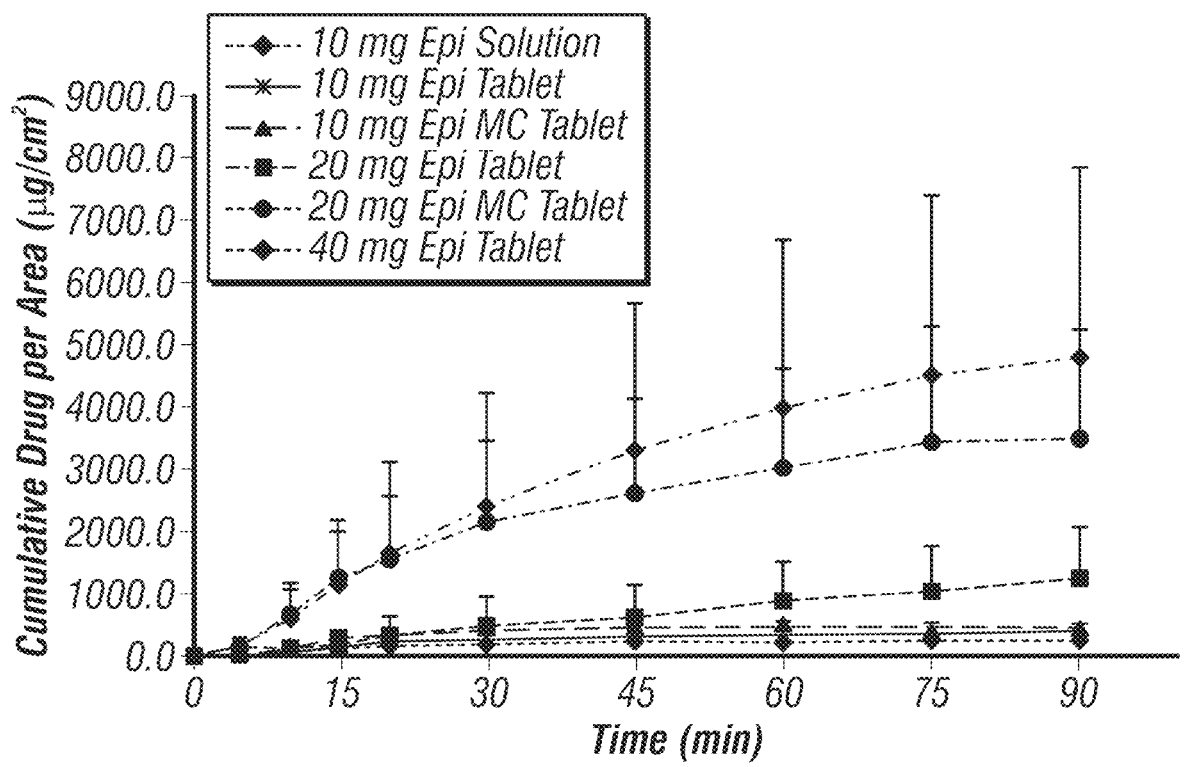
FIG. 10 shows the mean±SD (n=4) cumulative diffused epinephrine per sublingual mucosa area versus time.
Figure 11:
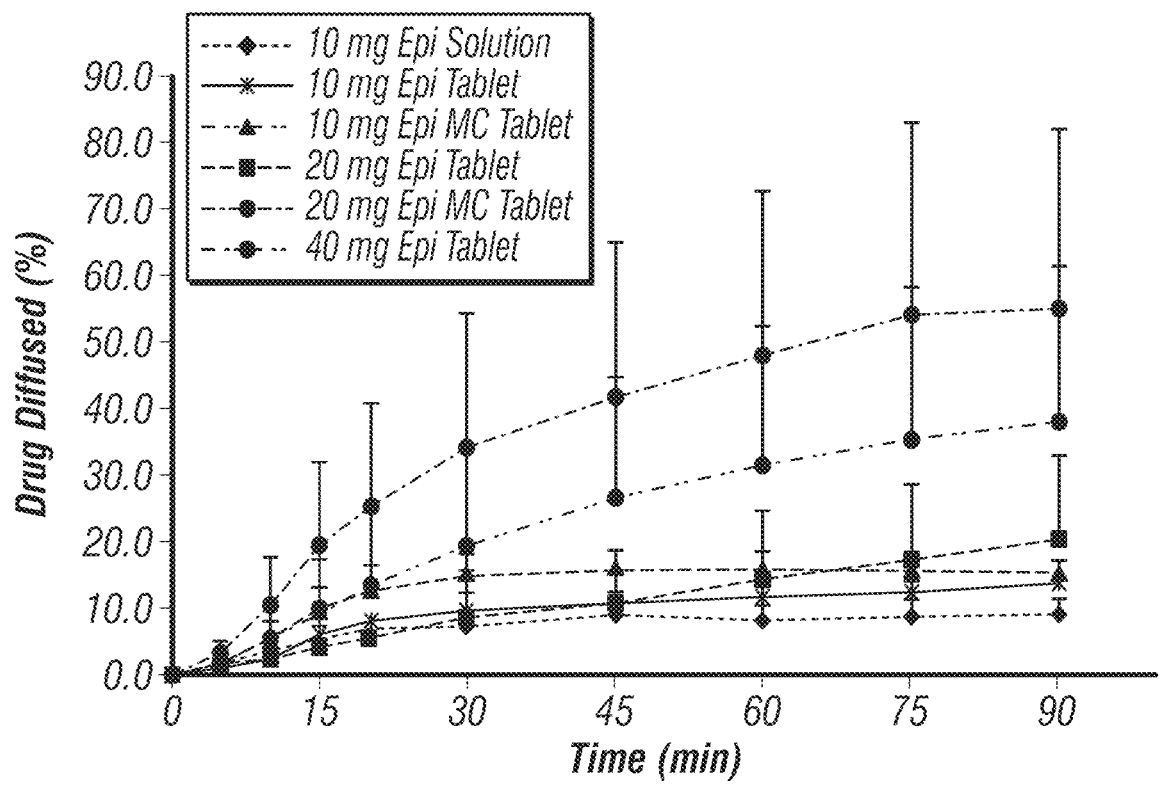
FIG. 11 shows the mean±SD (n=4) percentage of diffused epinephrine through sublingual mucosa versus time.

The mean±SD (n=4) cumulative diffused Epi per area and percentage of diffused Epi for each formulation through sublingual mucosa are shown in Tables 7 and 8, and illustrated in FIGS. 10 and 11, respectively.

TABLE 7

Mean ± SD (n = 4) cumulative diffused epinephrine per sublingual mucosa area ($\mu g/cm^2$) for each formulation through sublingual mucosa.

| Time (min) | 10 mg Epi Solution | 10 mg Epi Tablet | 10 mg Epi MC Tablet | 20 mg Epi Tablet | 20 mg Epi MC Tablet | 40 mg Epi Tablet |
|---|---|---|---|---|---|---|
| 5 | 24.5 ± 8.7 | 16.8 ± 12.7 | 32.5 ± 27.4 | 40.2 ± 44.9 | 176.1 ± 128.7 | 156.6 ± 159.4 |
| 10 | 80.3 ± 26.5 | 72.5 ± 50.5 | 161.5 ± 80.8 | 124.5 ± 123.1 | 639.1 ± 469.1 | 622.5 ± 559.3 |
| 15 | 143.0 ± 40.5 | 182.3 ± 104.3 | 296.7 ± 110.0 | 232.5 ± 217.1 | 1211.1 ± 808.0 | 1147.4 ± 1023.4 |
| 20 | 198.9 ± 56.5 | 248.0 ± 116.9 | 401.2 ± 110.1 | 341.7 ± 302.1 | 1588.9 ± 998.6 | 1689.4 ± 1437.7 |
| 30 | 219.8 ± 70.2 | 288.7 ± 88.7 | 465.5 ± 101.1 | 525.7 ± 444.6 | 2161.7 ± 1285.2 | 2415.0 ± 1834.7 |
| 45 | 273.8 ± 96.2 | 341.0 ± 37.6 | 499.0 ± 88.7 | 664.9 ± 501.1 | 2628.4 ± 1496.8 | 3311.4 ± 2321.8 |
| 60 | 248.7 ± 60.5 | 364.3 ± 75.9 | 488.9 ± 86.8 | 898.1 ± 643.1 | 3037.6 ± 1574.1 | 3989.8 ± 2648.3 |
| 75 | 266.1 ± 73.4 | 390.0 ± 47.8 | 479.5 ± 80.0 | 1072.8 ± 733.2 | 3435.1 ± 1828.8 | 4464.8 ± 2928.8 |
| 90 | 277.2 ± 80.8 | 430.1 ± 100.1 | 478.4 ± 58.9 | 1263.1 ± 807.6 | 3496.3 ± 1722.8 | 4795.7 ± 2988.2 |

TABLE 8

Mean ± SD (n = 4) percentage of diffused epinephrine (%) for each formulation through sublingual mucosa.

| Time (min) | 10 mg Epi Solution | 10 mg Epi Tablet | 10 mg Epi MC Tablet | 20 mg Epi Tablet | 20 mg Epi MC Tablet | 40 mg Epi Tablet |
|---|---|---|---|---|---|---|
| 5 | 1.1 ± 0.7 | 0.5 ± 0.4 | 1.0 ± 0.9 | 0.6 ± 0.7 | 2.8 ± 2.0 | 1.2 ± 1.3 |
| 10 | 3.1 ± 1.2 | 2.3 ± 1.6 | 5.1 ± 2.5 | 2.0 ± 1.9 | 10.0 ± 7.4 | 4.9 ± 4.4 |
| 15 | 5.0 ± 1.5 | 5.7 ± 3.3 | 9.3 ± 3.5 | 3.7 ± 3.4 | 19.0 ± 12.7 | 9.0 ± 8.0 |
| 20 | 6.5 ± 1.8 | 7.8 ± 3.7 | 12.6 ± 3.5 | 5.4 ± 4.7 | 24.9 ± 15.7 | 13.3 ± 11.3 |
| 30 | 7.1 ± 2.3 | 9.1 ± 2.8 | 14.6 ± 3.2 | 8.3 ± 7.0 | 33.9 ± 20.2 | 19.0 ± 14.4 |
| 45 | 8.7 ± 3.0 | 10.7 ± 1.2 | 15.7 ± 2.8 | 10.4 ± 7.9 | 41.3 ± 23.5 | 26.0 ± 18.2 |
| 60 | 8.0 ± 2.0 | 11.4 ± 2.4 | 15.4 ± 2.7 | 14.1 ± 10.1 | 47.7 ± 24.7 | 31.3 ± 20.8 |
| 75 | 8.5 ± 2.4 | 12.2 ± 1.5 | 15.1 ± 2.5 | 16.8 ± 11.5 | 53.9 ± 28.7 | 35.0 ± 23.0 |
| 90 | 8.6 ± 2.5 | 13.5 ± 3.1 | 15.0 ± 1.8 | 19.8 ± 12.7 | 54.9 ± 27.0 | 37.6 ± 23.5 |

The mean (±SD) Epi $JAUC_{0-90}$, Jmax, Tmax, J, P, and $t_L$ are shown in Table 9. Also, Epi J and P for each formulation are illustrated in FIGS. 12 and 13, respectively.

The mean Epi $JAUC_{0-90}$ and Jmax of 40 mg Epi tablets (264556.4±182820.3 $\mu g/cm^2$/min and 4795.7±2988.2 $\mu g/cm^2$, respectively) and 20 mg Epi MC tablets (211368.5±116025.1 $\mu g/cm^2$/min and 3526.8±1754.6 $\mu g/cm^2$, respectively) were not significantly different (p>0.05) from each other and 40 mg Epi tablets was significantly higher (p<0.05) than the rest of the formulations (FIG. 10 and Table 9).

Figure 12:
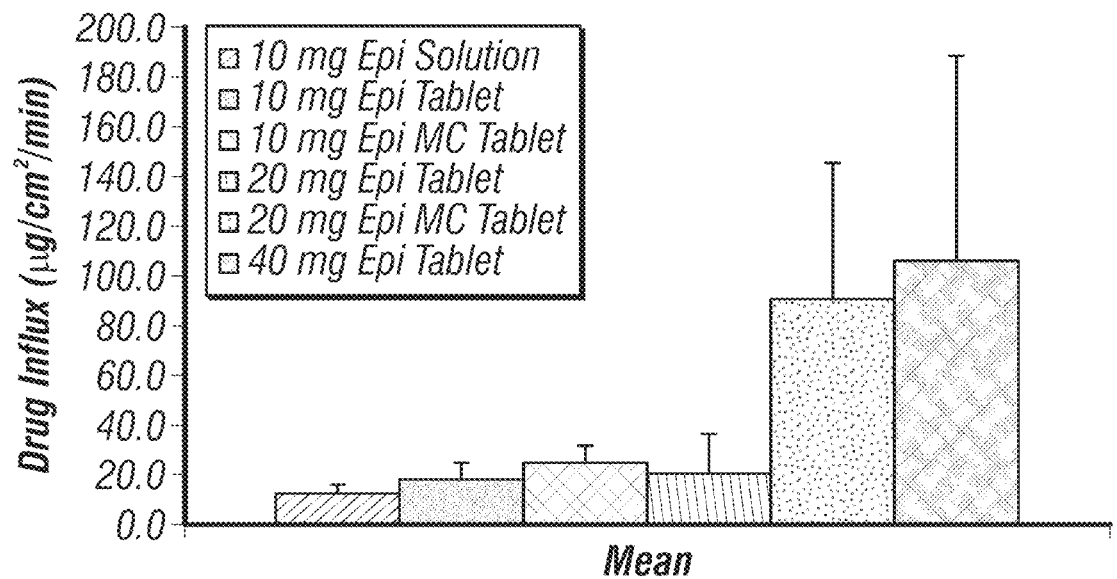
FIG. 12 shows the mean±SD (n=4) of epinephrine influx (J) through sublingual mucosa.

The Epi J of 40 mg Epi tablets (106.0±82.4 $\mu g/cm^2$/min) and 20 mg Epi MC tablets (91.1±54.6 $\mu g/cm^2$/min) were not significantly different (p>0.05) from each other but due to the high variability there were not significantly different (p>0.05) form 20 mg Epi tablets (19.9±16.0 $\mu g/cm^2$/min) and 10 mg Epi tablets (24.8±6.5 $\mu g/cm^2$/min) as well (FIG. 12 and Table 9). The Epi J of 40 mg Epi tablets was only significantly higher (p<0.05) than the 10 mg Epi solution (11.7±3.2 $\mu g/cm^2$/min) and 10 mg Epi tablets (17.1±6.7 $\mu g/cm^2$/min) (FIG. 12 and Table 9). The Epi $t_L$ was not significantly different (p>0.05) between all formulations (Table 9).

Figure 13:
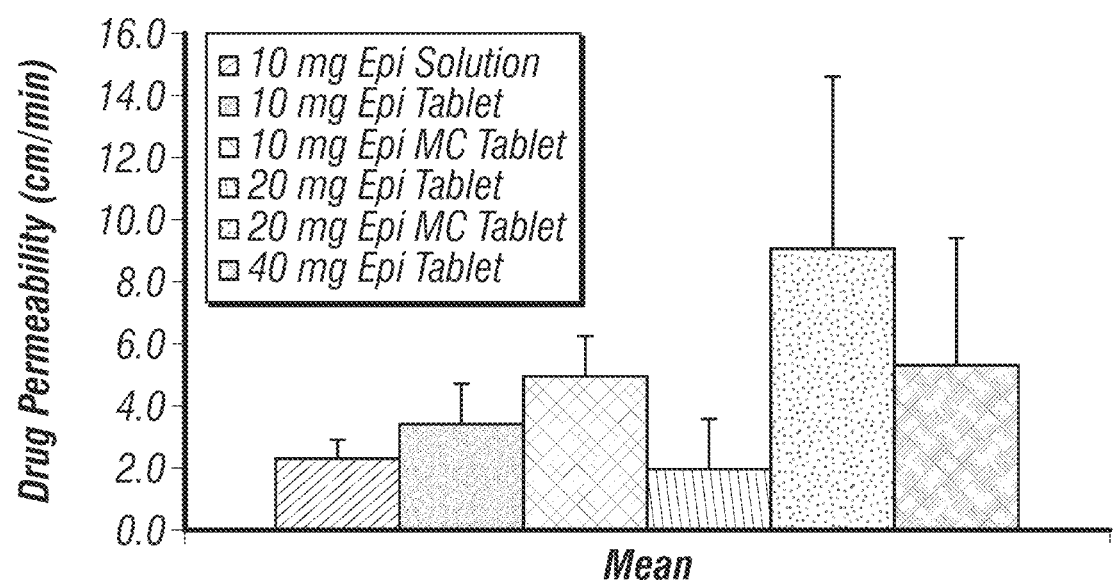
FIG. 13 shows the mean±SD (n=4) of epinephrine permeability (P) through sublingual mucosa.

The Epi P of 20 mg Epi MC tablets (9.1±5.5 cm/min) and 40 mg Epi tablets (5.3±4.1 cm/min) were not significantly different (p>0.05) from each other and 20 mg Epi MC tablets was significantly higher (p<0.05) than 20 mg Epi tablets (2.0±1.6 cm/min) (FIGS. 11 and 13, and Table 9).

All the diffusion parameters for both 10 mg Epi solution and 10 mg Epi ODT (Table 9) were not significantly different (p>0.05) from each other.

TABLE 9

Mean ± SD (n = 4) of epinephrine JAUC$_{0-90}$, Jmax, Tmax, J, P, and t$_L$ for each formulation through sublingual mucosa.

|  | 10 mg Epi Solution | 10 mg Epi Tablet | 10 mg Epi MC Tablet | 20 mg Epi Tablet | 20 mg Epi MC Tablet | 40 mg Epi Tablet |
|---|---|---|---|---|---|---|
| JAUC$_{0-90}$ (µg/cm$^2$/min) | 19325.8 ± 5599.3 | 26441.6 ± 5651.6 | 36799.7 ± 7226.5 | 60031.0 ± 43809.8 | 211368.5 ± 116025.1 | 264556.4 ± 182820.3 |
| Jmax (µg/cm$^2$) | 236.4 ± 101.9 | 436.7 ± 96.9 | 507.2 ± 81.4 | 1263.1 ± 807.6 | 3526.8 ± 1754.6 | 4795.7 ± 2988.2 |
| Tmax (min) | 75.0 ± 21.2 | 86.3 ± 7.5 | 48.8 ± 18.9 | 90.0 ± 0.0 | 82.5 ± 8.7 | 90.0 ± 0.0 |
| J (µg/cm$^2$/min) | 11.7 ± 3.2 | 17.1 ± 6.7 | 24.8 ± 6.5 | 19.9 ± 16.0 | 91.1 ± 54.6 | 106.0 ± 82.4 |
| P (cm/min) | 2.3 ± 0.6 | 3.4 ± 1.3 | 5.0 ± 1.3 | 2.0 ± 1.6 | 9.1 ± 5.5 | 5.3 ± 4.1 |
| t$_L$ (min) | 2.9 ± 0.4 | 5.8 ± 2.0 | 3.6 ± 1.5 | 5.1 ± 2.8 | 3.0 ± 2.4 | 5.2 ± 2.3 |

JAUC$_{0-90}$, area under the curve of diffused Epi per area versus time; Jmax, the maximum Epi diffused; Tmax, the time to reach Jmax; J, Epi influx; P, Epi permeability; t$_L$, lag time.

The JAUC, Jmax, J, P for 20 mg Epi MC tablets was not significantly different (p>0.05) from 40 mg Epi tablets. The reduction of EpiBit particles size close to the nano-size range increased EpiBit influx two folds, which presents a great potential for these reduced-sized Epi ODT to reduce the required Epi sublingual dose by half.

In Vivo Absorption Studies

The research was conducted according to current guidelines published by the Canadian Council on Animal Care[21] and was approved by the University of Manitoba Protocol Management and Review Committee.

Methods

Using a prospective, placebo-controlled, randomized, crossover study design, six New Zealand female white rabbits (mean±SD weight 3.6±0.1 Kg) were investigated on different study days at least four weeks apart, using a protocol described previously[10, 11]. Each rabbit received sublingually either Epi 40 mg, Epi MC 20 mg ODT, or placebo ODT (as a negative control). Epi 0.3 mg IM injection was given in the rabbit's thigh muscle from an EpiPen® as a positive control.

For the sublingual administration of tablets, the rabbit's mouth was opened using speculum and the tablet was placed underneath the tongue using a pair of flat forceps. A 0.1-0.2 mL volume of water was administered immediately after dosing to facilitate tablet disintegration. The rabbit's tongue was gently pressed for 2 minutes to prevent the rabbit from chewing or swallowing the tablet. At the end of the 2-minute immobilization time, the mouth was rinsed with 30-40 mL of water, in order to remove any insoluble tablet residue from the oral cavity.

Epi 0.3 mg was injected IM in the thigh using an EpiPen®, after which the solution remaining in the EpiPen® was evacuated into a plastic tube and frozen at −20° C., to be analyzed for Epi content using a reverse phase high performance liquid chromatography (HPLC) system (Waters Corp., Milford, Mass.) with ultra violet detection (UV) according USP method[19].

Measurement of Plasma Epinephrine Concentrations

An indwelling catheter (22 G 1", BD, Ontario, Canada) was inserted into an ear artery at least 30 minutes before dosing. A 2 mL blood sample was withdrawn immediately before dosing and at 5, 10, 15, 20, 30, 40, and 60 minutes afterwards.

All collected blood samples were transferred into Vacutainer plasma separation tubes containing EDTA (BD, Ontario, Canada), refrigerated within 1 hour of sampling, and centrifuged at 1600 g, 4° C. Plasma were transferred into appropriately labeled polypropylene tubes, and stored at −20° C. until analysis. Before analysis, plasma was thawed at room temperature and Epi was extracted by a solid-liquid extraction process, with an efficiency of 78%-83%. Epi concentrations were measured using HPLC system (Waters Corp., Milford, Mass.) with electrochemical detection (EC)[22-24]. Two calibration curves with two different Epi concentration ranges were prepared. The low range calibration curve was linear over the range of 0.1 to 1.0 ng/ml with a coefficient of variation of 0.4% at 0.1 ng/ml and 0.1% at 1.0 ng/ml. The high range calibration curve was linear over the range of 1.0 to 10.0 ng/ml with a coefficient of variation of 0.1% at 1.0 ng/ml and 0.1% at 10.0 ng/ml.

Data Analysis

The maximum plasma Epi concentration ($C_{max}$), the time at which $C_{max}$ was achieved ($T_{max}$), and the area under the plasma concentration versus time curves (AUC) were calculated from the plasma Epi concentration versus time plots of each individual rabbit using WinNonlin® 5.3 (Pharsight, Mountain View, Calif.). The AUC, $C_{max}$, and $T_{max}$ values for each rabbit were compared using ANOVA, ANCOVA and Tukey-Kramer multiple comparison tests using NCSS Statistical Analysis Software (NCSS, Kaysville, Utah). Differences were considered to be significant at p<0.05.

Results

The mean (±SD) of Epi dose injected using EpiPen® auto-injectors was 0.29±0.02 mg as calculated by multiplying the Epi concentration, measured in the solution remaining in the EpiPen® after injection, by the stated injected volume (0.3 mL).

Figure 14:
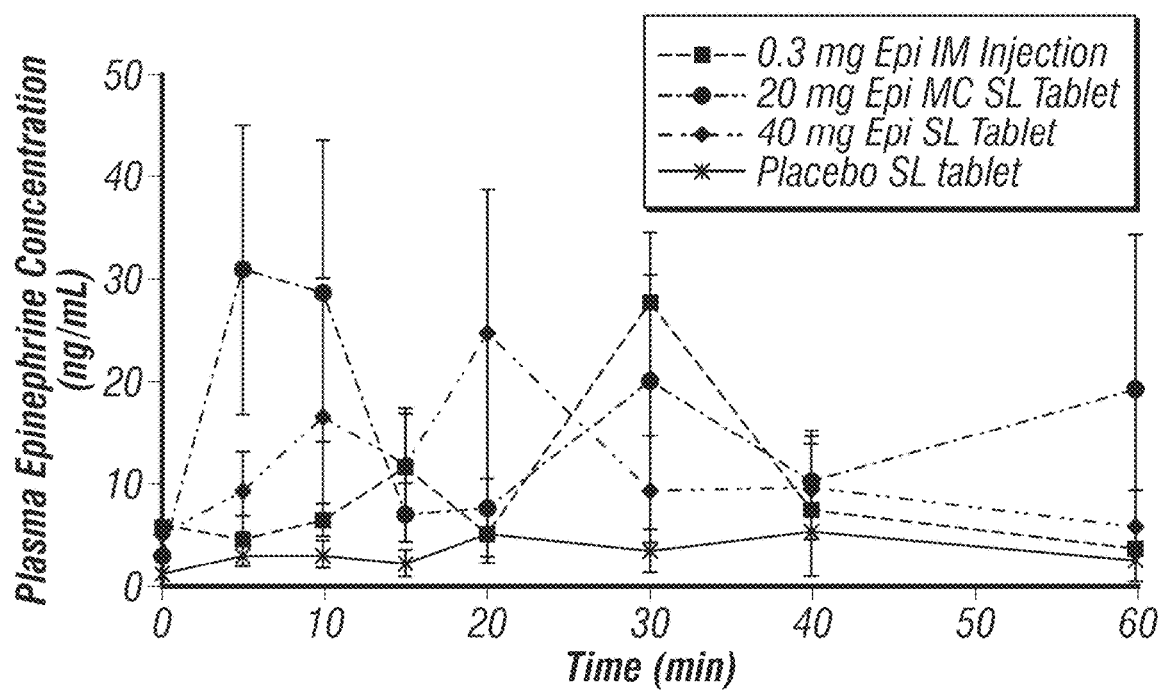
FIG. 14 shows the mean±SD plasma epinephrine concentration versus time plots (n=5) after administration of epinephrine by intramuscular (IM) injection, epinephrine microcrystals sublingual (SL) tablets, epinephrine sublingual (SL) tablets, or placebo sublingual tablets.

Mean (±SD) plasma Epi concentration versus time plots after the sublingual administration of placebo ODT, Epi 40 mg ODT, and Epi MC 20 mg ODT, and the IM injection of Epi 0.3 mg using EpiPen® are shown in FIG. 14. Mean (±SD) AUC, $C_{baseline}$ (endogenous E), $C_{max}$, and $T_{max}$ values after the sublingual administration of placebo ODT, Epi 40 mg ODT, and Epi MC 20 mg ODT, and Epi 0.3 mg IM injection are shown in Table 10. No adverse effects were observed.

Mean (±SD) AUC after the administration of Epi MC 20 mg ODT (942.0±243.7 ng/ml/min), Epi 40 mg ODT (678.0±149.0 ng/ml/min), and Epi 0.3 mg IM (592.0±122.3 ng/ml/min) did not differ significantly, but were significantly higher than after placebo ODT (220.1±78.0 ng/ml/min).

Mean (±SD) $C_{max}$ values after Epi MC 20 mg ODT (38.0±9.9 ng/ml), Epi 40 mg ODT (31.7±10.1 ng/ml) and Epi 0.3 mg IM (27.6±7.0 ng/ml) did not differ significantly, but were significantly higher than after placebo ODT (7.5±3.0 ng/ml).

Mean (±SD) $T_{max}$ after the sublingual administration of placebo ODT (33.3±17.5 min), Epi MC 20 mg ODT (28.0±29.3 min), and Epi 40 mg ODT (20.0±7.1 min), and IM injection of Epi 0.3 mg (30.0±0.0 min) did not differ significantly.

TABLE 10

Epinephrine bioavailability after sublingual administration of placebo, epinephrine and epinephrine nanocrystals tablets and epinephrine intramuscular injection in the thigh.

| Mean ± SD* | Placebo | Sublingual ODT | | IM Injection |
| --- | --- | --- | --- | --- |
| | | 40 mg Epi | 20 mg Epi MC | EpiPen ® |
| Epinephrine dose (mg) | 0 | 40.0 | 20.0 | 0.3 |
| AUC (ng/ml/min) | 220.1 ± 78.0 | 678.0 ± 149.0† | 942.0 ± 243.7† | 592.0 ± 122.3† |
| $C_{baseline}$ (ng/ml) | 1.1 ± 1.2 | 5.0 ± 3.0 | 2.9 ± 1.6 | 5.6 ± 1.9‡ |
| $C_{max}$ (ng/ml) | 7.5 ± 3.0 | 31.7 ± 10.1† | 38.0 ± 9.9† | 27.6 ± 7.0† |
| $T_{max}$ (min) | 33.3 ± 17.5 | 20.0 ± 7.1 | 28.0 ± 29.3 | 30.0 ± 0.0 |

*n = 5
†p < 0.05 from placebo tablet but not from each others.
‡p < 0.05 from placebo tablet but not from others.
AUC: area under the plasma concentration versus time curve;
$C_{baseline}$: Baseline plasma concentration (endogenous epinephrine);
$C_{max}$: maximum plasma concentration (mean ± SD of individual $C_{max}$ values from each rabbit, regardless of the time at which $C_{max}$ was achieved);
$T_{max}$: time at which maximum plasma epinephrine concentration was achieved (mean ± SD of individual $T_{max}$ values from each rabbit).

Discussion of Experiments

Previously, the Epi was delivered sublingually using rabbit's animal model. It was determined that 40 mg Epi, using EpiBit, is the bioequivalent sublingual dose using the novel ODT tablets[15, 16] to the recommended IM injection of 0.3 mg Epi given in the thigh muscle for adults[10, 11]. Also, the ODT formulations were developed to taste mask the bitter taste of Epi[25] and this ODT formulation was evaluated using electronic tongue[14]. This new taste-masked, sublingually administered 40 mg Epi ODT formulation was bioequivalent to 0.3 mg Epi IM injection as well[26].

In order to enhance the sublingual bioavailability of Epi, the particles size of EpiBit crystals were reduced up to 55 folds. Significant reduction in the drug particles' size results in increasing the saturation solubility, which increases the concentration gradients that promotes absorption, and dissolution rate of the drug that will ultimately increase its bioavailability, thus, resulting in a significant reduction in the required dose and any associated side effects[17, 23]. This is particularly important for the sublingual drug delivery due to the small saliva volume available for drug dissolution and the short sublingual residence time compared to the GIT.

Despite that the aim was to reduce the particles size of EpiBit to the nano-size (1000 nm or less), the size was reduced to a range that is very close to the nano-size range. It was very challenging to reach to a nanoosize range while not using a surfactant, which may need to be evaluated later, and by processing EpiBit for only one cycle to reduce any potential stress on EpiBit that can influence its stability[28]. The concentration of EpiBit suspension, the pressure applied, and the number of cycles were optimized to obtain the smallest particle size range with the lowest possible number of cycles.

The FT-IR spectra of EpiBit before and after processing for one cycle using Microfluidizer, LV-1, were similar, which indicates for the stability of the EpiBit during the particles size reduction process under these processing conditions (FIG. 1). Also, the drying step to obtain the reduced-sized EpiBit crystals was very efficient and no evidence in the FT-IR spectrum for any remaining isopropyl alcohol, which was used as a carrier to process EpiBit (FIG. 2).

The DSC spectra of EpiBit before and after processing were also similar with a single endothermic peak around 157° C. that indicates for the absence of any change in the purity and crystallinity of EpiBit (FIGS. 5A-5B).

The Scanning Electron Microscopy (SEM) images (FIGS. 5C-5D) of EpiBit before and after processing demonstrate clearly the change in EpiBit crystalline morphology from rectangular to spherical crystals with much smaller size.

The diffusion studies were conducted using dialysis membranes initially and then by using excised porcine sublingual mucosal membranes. It has been already established that the sublingual mucosa of pigs and rabbits are very similar to the human sublingual mucosa and were previously used for similar studies[29, 30]. Therefore, pigs' sublingual mucosa was selected for these diffusion studies and rabbits were always been selected in our previous studies for in vivo studies[10, 11, 26]. The sublingual mucosa of pigs has bigger surface area that is easy to be excised surgically for ex vivo studies and rabbits are easier to handle and house for in vivo studies.

Figure 15:
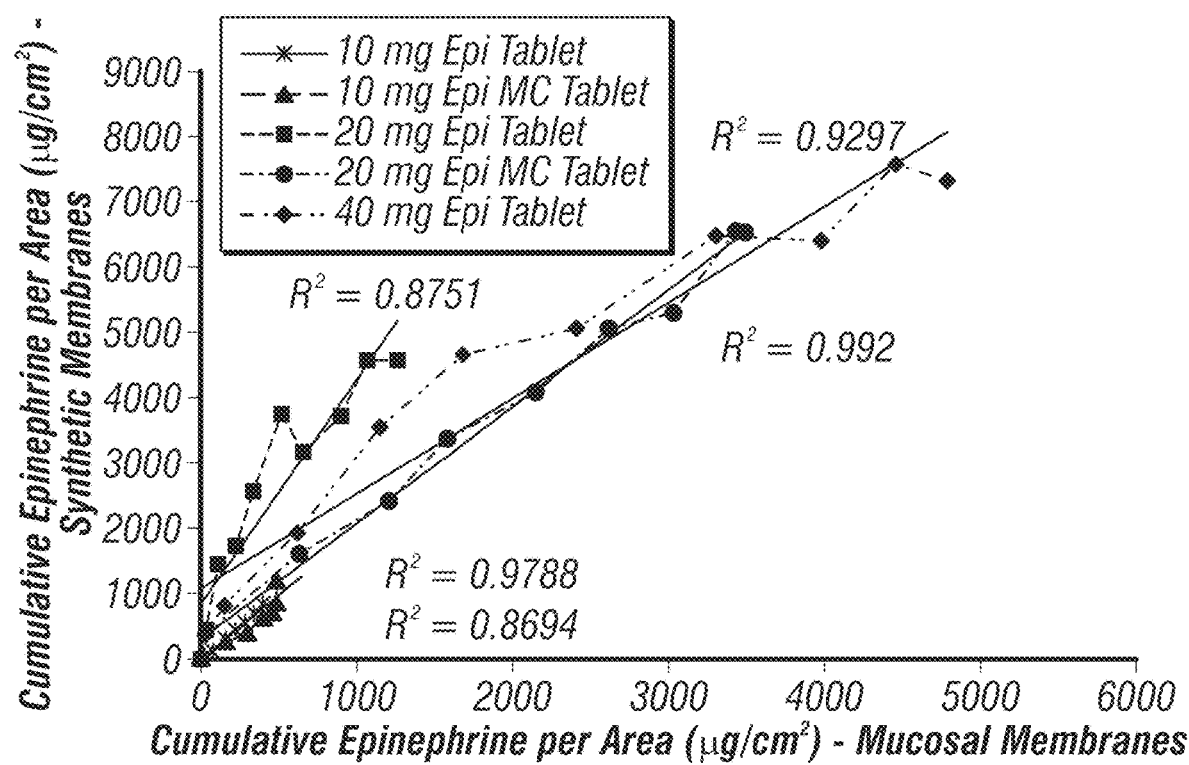
FIG. 15 shows the correlation between the cumulative diffused epinephrine per area through dialysis and excised sublingual membranes.

Results from both in vitro and ex vivo experiments were highly correlated, ($R^2 \geq 87$) (FIG. 15) and demonstrated that the percentage of Epi diffused from 20 mg Epi MC ODT was significantly higher than the rest of the formulations including 40 mg Epi ODT (FIGS. 7 and 11). This resulted in similar $JAUC_{0-90}$, Jmax, and influx (J) for both 20 mg Epi MC ODT and 40 mg Epi ODT, despite of the non-statistically different permeability, although higher, for 20 mg Epi MC ODT (Tables 6 and 9). Also, formulating EpiBit into the ODT tablet formulation did not pose any delay nor influenced EpiBit diffusion as shown from comparing the 10 mg Epi diffusion from solution and ODT (Table 9).

The significant reduction of the particles size of EpiBit increased its influx two folds, which presents a great potential for these micro-sized Epi ODT to reduce the required Epi sublingual dosed by half. Animal studies in rabbits have shown similar results.

This study demonstrates that reducing the particles size of EpiBit to almost to the nano-size range improved its diffusion from rapidly-disintegrating tablet formulation (ODT) by two folds. These micro-sized Epi ODT tablets have the potential to reduce the bioequivalent dose of sublingually administered Epi by 50%.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, epinephrine fine particles, epinephrine nanoparticles, epinephrine nanocrystals, epinephrine microparticles, epinephrine microcrystal s, pharmaceutical tablets, pharmaceutically-effective doses of epinephrine nanoparticles or nanocrystals or epinephrine microparticles or microcrystals, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

REFERENCE LIST

1. Kemp S F, Lockey R F, Simons F E. Epinephrine: the drug of choice for anaphylaxis. A statement of the World Allergy Organization. Allergy 2008; 63:1061-70.
2. McLean-Tooke A P, Bethune C A, Fay A C, Spickett G P. Adrenaline in the treatment of anaphylaxis: what is the evidence? Bmj 2003; 327:1332-5.
3. Simons K J, Simons F E. Epinephrine and its use in anaphylaxis: current issues. Curr Opin Allergy Clin Immunol 2010; 10:354-61.
4. Soar J, Pumphrey R, Cant A, Clarke S, Corbett A, Dawson P, et al. Emergency treatment of anaphylactic reactions— guidelines for healthcare providers. Resuscitation 2008; 77:157-69.
5. Simons F E. Epinephrine auto-injectors: first-aid treatment still out of reach for many at risk of anaphylaxis in the community. Ann Allergy Asthma Immunol 2009; 102:403-9.
6. Simons F E R. Lack of worldwide availability of epinephrine autoinjectors for outpatients at risk of anaphylaxis. Ann Allergy Asthma Immunol 2005; 94:534-8.
7. Bredenberg S, Duberg M, Lennernas B, Lennernas H, Pettersson A, Westerberg M et al. In vitro and in vivo evaluation of a new sublingual tablet system for rapid oromucosal absorption using fentanyl citrate as active substance. Eur J Pharm Sci 2003; 20:327-34.
8. Glover E D, Glover P N, Franzon M, Sullivan C R, Cerullo C C, Howell R M, et al. A comparison of a nicotine sublingual tablet and placebo for smoking cessation. Nicotine Tob Res 2002; 4:441-50.
9. Guez S. Efficacy of desensitization via the sublingual route in mite allergy. Chem Immunol Allergy 2003; 82:62-76.
10. Rawas-Qalaji M M, Simons F E, Simons K J. Sublingual epinephrine tablets versus intramuscular injection of epinephrine: Dose equivalence for potential treatment of anaphylaxis. J Allergy Clin Immunol 2006; 117:398-403.
11. Rawas-Qalaji M M, Simons F E, Simons K J. Epinephrine for the treatment of anaphylaxis: do all 40 mg sublingual epinephrine tablet formulations with similar in vitro characteristics have the same bioavailability? Biopharm Drug Dispos 2006; 27:427-35.
12. Saxena P, Salhan S, Sarda N. Sublingual versus vaginal route of misoprostol for cervical ripening prior to surgical termination of first trimester abortions. Eur J Obstet Gynecol Reprod Biol 2005.
13. Hoffman B B, Taylor P. Neurotransmission: The Autonomic and Somatic Motor Nervous Systems In: Hardman J G, Limbird L E, Gilman A G, editors. Goodman & Gilman's The Pharmacological Basis of Therapeutics. 9 ed. New York: McGraw-Hill Companies, Inc.; 2001. p. 115-53.
14. Rachid O, Simons F E, Rawas-Qalaji M, Simons K J. An electronic tongue: evaluation of the masking efficacy of sweetening and/or flavoring agents on the bitter taste of epinephrine. AAPS PharmSciTech 2010; 11:550-7.
15. Rawas-Qalaji M M, Simons F E, Simons K J. Fast-disintegrating sublingual epinephrine tablets: effect of tablet dimensions on tablet characteristics. Drug Dev Ind Pharm 2007; 33:523-30.
16. Rawas-Qalaji M M, Simons F E R, Simons K J. Fast-Disintegrating Sublingual Tablets: Effect of Epinephrine Load on Tablet Characteristics. AAPS PharmSciTech 2006; 7:Article 41.
17. Muller R H, Gohla S, Keck C M. State of the art of nanocrystals â€" Special features, production, nanotoxicology aspects and intracellular delivery. European Journal of Pharmaceutics and Biopharmaceutics; 78:1-9.
18. USP/NF. Physical Tests: Uniformity of Dosage Units (905). 31/26 ed. Rockville, Md.: United States Pharmacopeial Convention, Inc.; 2008.
19. USP/NF. Official Monograph: Epinephrine Injection. 31/26 ed. Rockville, Md.: United States Pharmacopeial Convention, Inc.; 2008.
20. USP/NF. Physical Tests: Tablet Friability (1216). 31/26 ed. Rockville, Md.: United States Pharmacopeial Convention, Inc.; 2008.
21. Olfert E D, Cross B M, McWilliam A A. Guide to the care and use of experimental animals. 2 ed. Ottawa: Canadian Council on Animal Care; 1993.
22. Hjemdahl P. Inter-laboratory comparison of plasma catecholamine determinations using several different assays. Acta Physiol Scand Suppl 1984; 527:43-54.
23. Hjemdahl P. Catecholamine measurements in plasma by high-performance liquid chromatography with electrochemical detection. Methods Enzymol 1987; 142:521-34.
24. Ganhao M F, Hattingh J, Hurwitz M L, Pitts N I. Evaluation of a simple plasma catecholamine extraction procedure prior to high-performance liquid chromatography and electrochemical detection. J Chromatogr 1991; 564:55-66.
25. Rachid O, Rawas-Qalaji M, Simons F E, Simons K J. Rapidly-disintegrating sublingual tablets of epinephrine: role of non-medicinal ingredients in formulation development. Eur J Pharm Biopharm 2012; 82:598-604.
26. Rachid O, Rawas-Qalaji M M, Simons F E, Simons K J. Epinephrine (adrenaline) absorption from new-generation, taste-masked sublingual tablets: a preclinical study. J Allergy Clin Immunol 2013; 131:236-8.
27. Liu Y, Sun C, Hao Y, Jiang T, Zheng L, Wang S. Mechanism of dissolution enhancement and bioavailability of poorly water soluble celecoxib by preparing stable amorphous nanoparticles. J Pharm Pharm Sci 2010; 13:589-606.
28. Ma Q, Sun H, Che E, Zheng X, Jiang T, Sun C, et al. Uniform nano-sized valsartan for dissolution and bioavailability enhancement: Influence of particle size and crystalline state. Int J Pharm 2013; 441:75-81.
29. Dali M M, Moench P A, Mathias N R, Stetsko P I, Heran C L, Smith R L. A rabbit model for sublingual drug delivery: comparison with human pharmacokinetic studies of propranolol, verapamil and captopril. J Pharm Sci 2006; 95:37-44.
30. Ong C M, Heard C M. Permeation of quinine across sublingual mucosa, in vitro. Int J Pharm 2009; 366:58-64.

What is claimed is:

1. A pharmaceutical composition formulated as a tablet for buccal or sublingual administration comprising approximately 10 mg to approximately 40 mg of stabilized epinephrine bitartrate microcrystals, the stabilized epinephrine bitartrate microcrystals having a spherical shape, the spherical shape formed when raw epinephrine bitartrate particles having a rectangular shape undergo a morphological change when reduced in size to form the stabilized epinephrine bitartrate microcrystals of the pharmaceutical composition.

2. The pharmaceutical composition according to claim 1, further comprising at least one of a surfactant, a penetration enhancer, a mucoadhesive, a filler, a lubricant, a disintegrant, a taste enhancer, and a sweetening agent and mouthfeel enhancer.

3. The pharmaceutical composition according to claim 1, wherein the stabilized epinephrine bitartrate microcrystals are formed from raw epinephrine bitartrate particles having been reduced to a particle size of 2.5 μm or less.

4. The pharmaceutical composition according to claim 1, formulated as a tablet for buccal or sublingual administration comprising 20 mg stabilized epinephrine bitartrate microcrystals.

5. The pharmaceutical composition according to claim 2, comprising a filler, a lubricant, and a disintegrant, wherein the filler is microcrystalline cellulose, the lubricant is magnesium stearate, and the disintegrant is a hydroxypropyl ether of cellulose.

6. The pharmaceutical composition according to claim 5, further comprising a taste enhancer and a sweetening agent and mouthfeel enhancer, wherein the taste enhancer is citric acid, and the sweetening agent and mouthfeel enhancer is mannitol.

7. A pharmaceutical composition formulated as a tablet for buccal or sublingual administration having an active ingredient consisting of 10 mg to 40 mg stabilized epinephrine bitartrate microcrystals, the stabilized epinephrine bitartrate microcrystals having a spherical shape, the spherical shape formed when raw epinephrine bitartrate particles undergo a morphological change when reduced in size to form the stabilized epinephrine bitartrate microcrystals of the pharmaceutical composition.

8. The pharmaceutical composition according to claim 7, wherein the stabilized epinephrine bitartrate microcrystals are formed from raw epinephrine bitartrate particles having been reduced to a particle size of 2.5 μm or less.

9. The pharmaceutical composition according to claim 7, further comprising at least one of a surfactant, a penetration enhancer, a mucoadhesive, a filler, a lubricant, a disintegrant, a taste enhancer, and a sweetening agent and mouthfeel enhancer.

10. The pharmaceutical composition according to claim 7, formulated as a tablet for buccal or sublingual administration having an active ingredient consisting of 20 mg stabilized epinephrine bitartrate microcrystals.

11. The pharmaceutical composition according to claim 9, comprising a filler, a lubricant, and a disintegrant, wherein the filler is microcrystalline cellulose, the lubricant is magnesium stearate, and the disintegrant is a hydroxypropyl ether of cellulose.

12. The pharmaceutical composition according to claim 11, further comprising a taste enhancer and a sweetening agent and mouthfeel enhancer, wherein the taste enhancer is citric acid, and the sweetening agent and mouthfeel enhancer is mannitol.

* * * * *